(12) United States Patent
Huang

(10) Patent No.: US 8,900,813 B2
(45) Date of Patent: Dec. 2, 2014

(54) CIP2A AS A BIOMARKER IN DETECTION OF CERVICAL CANCER

(75) Inventor: Lisa P. Huang, Princeton, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 308 days.

(21) Appl. No.: 13/199,019

(22) Filed: Aug. 17, 2011

(65) Prior Publication Data

US 2012/0070837 A1    Mar. 22, 2012

Related U.S. Application Data

(60) Provisional application No. 61/401,661, filed on Aug. 17, 2010.

(51) Int. Cl.
  *C12Q 1/68* (2006.01)
  *G01N 33/566* (2006.01)
  *G01N 33/574* (2006.01)

(52) U.S. Cl.
  CPC ........ *G01N 33/57411* (2013.01); *C12Q 1/6886* (2013.01)
  USPC ............................................ 435/6.12; 436/501

(58) Field of Classification Search
  None
  See application file for complete search history.

(56) References Cited

U.S. PATENT DOCUMENTS

| | | | |
|---|---|---|---|
| 6,709,832 B1 | 3/2004 | Von Knebel Doeberitz | |
| 7,045,292 B2 | 5/2006 | Mai | |
| 7,157,233 B2 * | 1/2007 | Fischer et al. | 435/6.12 |
| 7,186,514 B2 | 3/2007 | Zavada | |
| 7,306,926 B2 | 12/2007 | Doeberitz | |
| 2005/0186215 A1 | 8/2005 | Kwok | |

OTHER PUBLICATIONS

Huang et al. (Cancer Biomarkers 8, 2010, 309-317, abstract only).*
Junttila, et al, CIP2A Inhibits PP2A in Human Malignancies, Cell, Jul. 13, 2007, pp. 51-62, Issue130, Elsevier Inc.
Herbert, et al, Screen-detected invasive cervical carcinoma and its clinical significance during the introduction of organized screening, BJOG, Apr. 7, 2009; pp. 854-859, vol. 116.
Zanagnolo, et al, Surveillance Procedures for Patients With Cervical Carcinoma: A Review of the Literature, Int Journal Gynecol Cancer, Feb. 2009; pp. 194-201,vol. 19, No. 2, IGCS and ESGO.
Kim, et al, Aberrant Cell Cycle Regulation in Cervical Carcinoma, Yonsei Medical Journal, Jul. 2005, pp. 597-613, vol. 46, Issue 5.
Come, et al, CIP2A Is Associated with Human Breast Cancer Aggressivity, Aug. 11, 2009, pp. 5092-5100, vol. 15.
Teng, et al, CIP2A Is a Predictor of Poor Prognosis in Colon Cancer, J Gastro Intest Surgery, Feb. 11, 2012, published online by Springer.
Li, et al, CIP2A Is Overexpressed in Gastric Cancer and Its Depletion Leads to Impaired Clonogenicity, Senescence, or Differentiation of Tumor Cells, Clin Cancer Res, Published online Jun. 16, 2008;14: pp. 3722-3728.
Wang, et al, CIP2A is over-expressed in acute myeloid leukaemia and associated with HL60 cells proliferation and differentiation, International Journal of Laboratory Hematology, Oct. 27, 2010, pp. 290-298, vol. 33.
Hoo, et al, Cloning and characterization of a novel 90 kDa 'companion' auto-antigen of p62 overexpressed in cancer, Oncogene Apr. 26, 2002, pp. 5006-5015, vol. 21, Nature.
Depuydt, et al, Improved endocervical sampling and HPV viral load detection by Cervex-Brush Combi, Cytopathology, May 19, 2006, pp. 374-381, vol. 17, Blackwell Publishing Ltd.
Junttila, et al, Mechanisms of MYC stabilization in human malignancies, Cell Cycle, Mar. 1, 2008, pp. 592-596 vol. 7: Issue 5, Landes Bioscience.
Klapproth, et al, Advances in the understanding of MYC-induced lymphomagenesis, British Journal of Haematology, 2010, Blackwell Publishing Ltd.
Wentzemnsen, et al, Identification of High-Grade Cervical Dysplasia by the Detection of p16INK4a in Cell Lysates Obtained From Cervical Samples, Cancer, 2006; pp. 7-13 vol. 107: Issue 23, 2006 American Cancer Society.
Arbyn, et al, How to evaluate emerging technologies in cervical cancer screening?, Int J Cancer. Dec. 1, 2009; pp. 2489-2496, vol. 125(11).
Eichhorn, et al, Protein phosphatase 2A regulatory subunits and cancer, Biochimica, Jun. 3, 2008, Biophysica Actam, pp. 1-15, vol. 1795.
Kanta, et al, Topoisomerase IIa gene amplification in gastric carcinomas: correlation with the HER2 gene. An immunohistochemical, immunoblotting, and multicolor fluorescence in situ hybridization studyB, Human Pathology May 18, 2006, pp. 1333-1343, vol. 37.

* cited by examiner

*Primary Examiner* — Stephanie K Mummert
(74) *Attorney, Agent, or Firm* — Siu K. Lo; Christina M. Segro, Esq.

(57) ABSTRACT

The present invention provides methods and compositions for detecting cervical cancer in a human. The present invention provides CIP2A as a biomarker detectable in a biological sample from cervix of an individual, an increased expression of same is an indication of cervical cancer in the individual. CIP2A mRNA or protein can both serve as reliable biomarkers. In one embodiment, the present invention provides a combined use of CIP2A with at least one additional biomarker selected from the group consisting of Ki67, TOP2A, MCM2, MCM5, p14$^{ARF}$ and p16$^{INK4a}$, to better serve as a detection means for cervical cancer. The present invention provides a reliable and accurate assay methods and compositions which may be used for detecting cervical cancer in an individual with a high sensitivity and specificity. The present assay provides a novel use of CIP2A as a tool for early detection of cervical cancer in humans.

16 Claims, 21 Drawing Sheets

CIP2A AS A BIOMARKER IN DETECTION OF CERVICAL CANCER

CROSS-REFERENCE TO RELATED APPLICATION

This application claims the benefit under 35 U.S.C. §119(e) to U.S. Provisional Application No. 61/401,661 filed Aug. 17, 2010, the contents of which are incorporated by reference herein in its entirety.

BACKGROUND OF THE INVENTION

Cervical cancer is the second most common cause of cancer death in developing nations, with about 370,000 new cases annually having a 50% mortality rate. In the past five decades, there has been a 75% decrease in incidence and mortality from cervical cancer in developed nations. Most of this decrease is attributed to the effective institution of cervical cancer screening programs, including regular Pap tests. There are several known risk factors for cervical cancer. An important risk factor for cervical cancer is the infection with a virus called HPV (human papillomavirus). HPV infection is a necessary factor in the development of nearly 70% of cases of cervical cancer. Because the underlying causes for cervical cancer are complex, identifying a reliable biomarker for this deadly disease has been elusive.

Early diagnosis for cervical cancer and prompt treatment cure nearly all cases of cervical dysplasia and neoplasia. The five year survival rate for patients with stage I cervical cancer is 80% or more. The five year survival rate drops to about 60% for patients with stage II cervical cancer and then drops to about 32% and 15% for those with stage III and stage IV cervical cancer, respectively. In order to ensure that cervical cancer is detected early, repeated Pap tests are recommended. However, cervical cytology is expensive, and requires Board-certified pathologists to review one by one and interpret the results from Pap smears.

There are several reports regarding different purported biomarkers for cervical cancer. U.S. Pat. No. 7,157,233 discloses many cell cycle regulation genes (i.e., S-phase genes) including $p14^{ARF}$, $p21^{waf1}$, Topo2A, and cyclin E as potential biomarkers for cervical dysplasia and neoplasia. U.S. Pat. No. 7,045,292 discloses an association between increased c-myc and cyclin D2 and Chronic Lymphocytic Leukemia. U.S. Pat. No. 7,186,514 discloses a new gene (i.e., MN gene) present in the chromosomal DNA that may have potential implications in tumorigenicity in many tissues, such as cervical tissue. U.S. Patent No. 2005/0186215 discloses the identification of a novel human gene (i.e., CUDR) as a biomarker in human cancer. All of these studies have not utilized sufficient clinical tissues from cervical cancer patients, and there is a lack of clinical validation. Furthermore, these genes represent unique cell cycling key regulators shared by many normal and tumor cells (i.e., not unique for cervical cancer).

U.S. Pat. No. 6,709,832 discloses another cell cycle regulatory protein (i.e., $p16^{INK4a}$). Using paraffin sections, these authors discovered that $p16^{INK4a}$ is over-expressed in cervical biopsies of dysplastic cells (i.e., CIN I, II and III) as well as in invasive carcinomas. The over-expression of $p16^{INK4a}$ seems to increase with the degree of dysplasia towards the invasive carcinoma. It can take 10 years or longer for cervical dysplasia to develop into cervical cancer. Because $p16^{INK4a}$ peaks at around CIN III (i.e., precancerous stage) (See, Table 2 of '832 patent) and that not all CIN III females will progress into invasive carcinoma (i.e., cancerous stage), it suggests additional factor(s) other than $p16^{INK4a}$ may contribute to the progression of cervical cancer. The role of $p16^{INK4a}$ as biomarker requires further clinical validation. U.S. Pat. No. 7,306,926 further discloses a method of using a solubilized cervical sample to measure $p16^{INK4a}$ and determining the elevated levels as a means of diagnosis and detection of cervical cancer. The commercial utility of this technology remains to be validated. To date, $p16^{INK4a}$ is the only commercially available biomarker for cervical cancer.

Accordingly, there exists a critical and continuing need to identify novel molecular biomarkers and develop them into clinical diagnostic assays for cervical cancer detection. There exists also a demand for a reliable biomarker that has high sensitivity and specificity. The present invention cures all the prior art deficiencies and provides a method of using CIP2A as a biomarker and its combined usage with additional biomarkers for the detection and diagnosis of cervical cancer. The present assay provides a high sensitivity and specificity of over 90%.

SUMMARY OF THE INVENTION

In one aspect, the present invention provides a method of detecting cervical cancer in a human, comprising the steps of: (a) obtaining a cervical sample from a human; and (b) detecting an expression level of CIP2A in said cervical sample, wherein an increase in said expression level is indicative of cervical cancer in said human.

In one preferred aspect, the cervix sample is obtained with a swab. The cervix sample may be a tissue.

In another preferred aspect, the human is suspected of suffering from cervical cancer, or is suffering from cervical cancer.

In another aspect, the detecting step is performed by qRT-PCR. The detecting step may also be performed by Western blot analysis. CIP2A expression level may be a mRNA or a protein. Preferably, CIP2A is a mRNA.

In another aspect, the present invention provides a method of detecting cervical cancer in a human, comprising the steps of: (a) obtaining a cervical sample from a human; and (b) detecting an expression level of CIP2A in said cervical sample; (c) detecting an expression level of an additional biomarker selected from the group consisting of Ki67, TOP2A, MCM2, MCM5, $p14^{ARF}$, and $p16^{INK4a}$ in said cervical sample, wherein an increase in expression level of CIP2A and an increase expression level of said additional biomarker is indicative of cervical cancer in said human.

In another aspect, the present invention provides a method of detecting cervical cancer in a human, wherein the increase in expression level of CIP2A and the increase expression level of said additional biomarker provide an assay sensitivity of at least 90%.

In another aspect, the present invention provides a combined use CIP2A with an additional biomarker of Ki67, TOP2A, MCM2, MCM5, $p14^{ARF}$, or $P16^{INK4a}$.

In another aspect, the present invention provides a kit for detecting cervical cancer in a human, comprising: (a) a pair of primer set specific for CIP2A mRNA, when used in an qRT-PCR reaction, detect mRNA expression level of CIP2A; and (b) an instruction for use of a forward primer and a reverse primer to detect said mRNA expression level of CIP2A in said cervical sample.

In another preferred aspect, the present invention further comprising (c) a swab for collecting a cervical sample from a human. Preferably, the present invention further comprising (c') a chemical agent for isolating RNA from said cervical sample. The chemical agent may include guanidinium thiocyanate, phenol-chloroform and the like.

In another aspect, the present invention provides a kit for detecting cervical cancer in a human, comprising: (a) a swab for collecting a cervical sample from a human; (b) a chemical agent for isolating protein from said cervical sample; (c) an anti-CIP2A antibody, wherein said anti-CIP2A antibody, when used in a Western blot assay, detect protein expression level of CIP2A; and (d) an instruction for use of said anti-CIP2A antibody to detect said protein expression level of CIP2A in said cervical sample.

DETAILED DESCRIPTION OF THE INVENTION

Figure 1A:
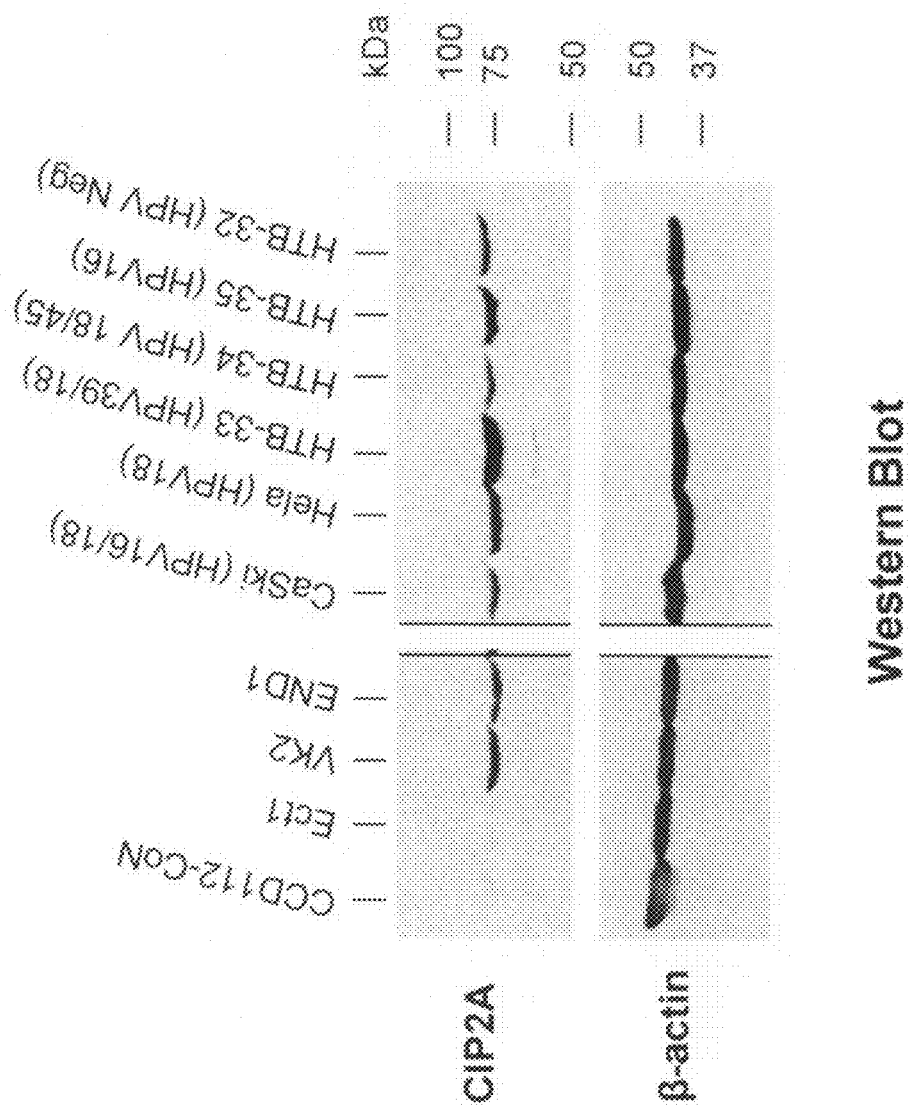
FIG. 1A depicts CIP2A protein expression in various cancer cell lines in a Western blot analysis.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions

The following terms shall have the meanings as defined hereunder:

As used herein, the term "biological sample" refers to a body sample in which biomarkers can be detected. A biological sample includes, but is not limited to, cervical swab, cervical tissues, cervical section, and biopsies of cervix (such as Pap smear) collected by cervical brush, spatula, or broom.

As used herein, the term "cervical cancer" refers to neoplasia of the cervix or cervical area and is intended to include, but not be limited to, squamous cell carcinoma, adenocarcinoma, adenosquamous carcinoma, small cell carcinoma and the like that occur in the cervix or cervical area.

As used herein, the term "cervix" refers to the lower part of the uterus and is intended to encompass the uterine cervix, endocervix and exocervix (i.e., ectocervix).

As used herein, the term "cervical sample" refers to tissues or cells collected from cervix. An example of cervical sample is Pap smear.

As used herein, the term "swab" refers to an instrument used to collect a biological sample. A swab includes, but is not limited to, a brush, spatula, broom and the like.

As used herein, the term "expression level" refers to expression of either mRNA or protein when such expression is measured quantitatively.

As used herein, the term "relative expression level" refers to mRNA expression levels after normalization with a housekeeping gene (e.g. GAPDH or β-actin).

As used herein, the term "relative expression ratio" refers to either mRNA expression level or protein expression level in cervical cancer tissues or cells in comparison to those mRNA or protein expression levels in normal cervical tissues or cells.

As used herein, the term "detect an expression level" refers to measuring or estimating either mRNA expression or protein expression.

As used herein, the term "increased expression level" refers to increased mRNA expression level or protein expression level. For purposes of this application, minimal mRNA expression level of CIP2A is observed in normal cervical tissues (N=23). An arbitrary value of a relative minimum expression level of approximately 1.2 (based on 23 patients in this application) is used as a reference to determine if there is an increased expression level. For example, an increased expression level of CIP2A mRNA is >1.2. Also, for purposes of this application, no detectable CIP2A protein is observed in our Western blot analysis in normal cervical tissues. CIP2A protein is only found to be present (i.e., increased from normal expression level) in cervical cancer tissue.

As used herein, the term "qRT-PCR" refers to quantitative reverse transcription-polymerase chain reaction.

As used herein, the term "CIP2A" (also known as Cancerous Inhibitor of PP2A or p90) refers to the protein (NCBI Accession No: NP_065941) that inhibits PP2A tumor suppressor activity and the CIP2A protein is encoded by the KIAA1524 gene (NCBI Accession No: BC136371).

As used herein, the term "PP2A" refers to protein-phosphatase 2 (also known as PP2). PP2A is an enzyme in humans that is encoded by the PPP2CA gene. Structurally, PP2A consists of three (3) subunits: (i) structural A and (ii) catalytic C subunits, and (iii) a regulatory B subunit.

As used herein, the term "PPP2CA" refers to serine/threonine-protein phosphatase 2A catalytic subunit alpha isozyme (NCBI Accession No: NP_002706.1). PPP2CA is a protein that is a component of the PP2A catalytic subunit and in humans is encoded by the PPP2CA gene (NCBI Accession No: NM_002715.2).

As used herein, the term "PPP2R1A" refers to serine/threonine-protein phosphatase 2A 65 kDa regulatory subunit A alpha isoform (NCBI Accession No: NP_055040.2). PPP2R1A is a protein that is a component of the constant regulatory subunit of PP2A and in humans is encoded by the PPP2R1A gene (NCBI Accession No: NM_014225.5).

As used herein, the term "PPP2R1B" refers to serine/threonine-protein phosphatase 2A 65 kDa regulatory subunit A beta isoform (NCBI Accession No: NP_859050.1). It is a protein that is a component of the constant regulatory subunit of PP2A and in humans is encoded by the PPP2R1B gene (NCBI Accession No: NM_181699.2).

As used herein, the term "PPP2R5A" refers to serine/threonine-protein phosphatase 2A 56 kDa regulatory subunit alpha isoform (NCBI Accession No: NP_006234.1).

It is a protein that is a component of the regulatory PP2A regulatory subunit B family and in humans is encoded by the PPP2R5A gene (NCBI Accession No: NM_006243.2).

As used herein, the term "PPP2R5C" refers to serine/threonine-protein phosphatase 2A 56 kDa regulatory subunit gamma isoform (NCBI Accession No: NP_001155197.1). It is a protein that is a component of the PP2A regulatory subunit B family and in humans is encoded by the PPP2R5c gene (NCBI Accession No: NM_178587.2).

As used herein, the term "PPP2R4" refers to serine/threonine-protein phosphatase 2A regulatory subunit (NCBI Accession No: NP_821068.1) a protein that is part of the regulatory subunit of PP2A and in humans is encoded by the PPP2R4 gene (NCBI Accession No: NM_178003.1).

As used herein, the term "c-myc" refers to an oncogene protein (NCBI Accession No: NP_002458.2) encoded by the c-myc gene (NM_002467.4).

As used herein, the term "Ki67" (also known as antigen Ki-67 or MK167) refers to a nuclear protein associated with cellular proliferation. Ki67 protein (NCBI Accession No. NP_002408.3) in humans is encoded by the MK167 gene (NCBI Accession No: AJ567755.1).

Ki67 is shown to associate with ribosomal RNA transcription, and inactivation of Ki67 is hypothesized to lead to inhibition of ribosomal RNA synthesis.

As used herein, the term "TOP2A" (NCBI Accession No: NM_001067.2) refers to the gene that encodes DNA topoisomerase 2-alpha (NCBI Accession No: NP_001058.2) an enzyme that controls and alters the topologic states of DNA during transcription.

As used herein, the term "MCM2" refers to a mini-chromosome maintenance protein (NCBI Accession No: NP_004517.2) involved in the initiation of eukaryotic genome replication and that is believed to be involved in the formation of replication forks and in the recruitment of other DNA replication related proteins that is encoded by the MCM2 gene (NCBI Accession No: NM_004526.2).

As used herein, the term "MCM5" refers to a mini-chromosome maintenance protein (NCBI Accession No: NP_006730.2) and DNA replication licensing factor MCM5 that is believed to participate in cell cycle regulation and that is encoded by the MCM5 gene (NCBI Accession No: NM_006739.3).

As used herein, the term "p16$^{INK4a}$" (also known as CDKN2A) refers to a cyclin-dependent kinase inhibitor 2A (NCBI Accession No. NP_478102.1). P16$^{INK4a}$ inhibits CDK4 and is a tumor suppressor protein. P16$^{INK4a}$ protein in humans is encoded by the CDKN2A gene (NCBI Accession No: NM_000077.3). P16$^{INK4a}$ plays an important role in regulating cell cycle, and mutations in p16$^{INK4a}$ are speculated to increase the risk of developing a variety of cancers.

As used herein, the term "p14$^{ARF}$" (also known as p14) refers to a tumor suppressor gene (NCBI Accession No. AAP35666.1). Both p14$^{ARF}$ and p16$^{INK4a}$ are involved in cell cycle regulation. p14$^{ARF}$ protein (NP_47812.1) inhibits mdm2, thus promoting p53, which promotes p21 activation, which then binds and inactivates certain cyclin-CDK complexes, which would otherwise promote transcription of genes that would carry the cell through the G1/S checkpoint of the cell cycle. Loss of p14$^{ARF}$ by a homozygous mutation in the CDKN2A (INK4A) gene will lead to elevated levels in mdm2 and, therefore, loss of p53 function and cell cycle control.

As used herein, the term "CYP21A" refers to a member of the cytochrome P450 superfamily of enzymes which hydroxylates steroids at the 21 position (NCBI Accession No. NP_000491.2).

As used herein, the term "IRF4" refers to interferon regulatory factor 4 (NCBI Accession No. NM_002460.2), a protein that in humans is encoded by the IRF4 gene (NCBI Accession No. NP_002451.2) and is also known as MUM1 and LSIRF.

As used herein, the term "biomarker" refers to an indicator of the presence of a disease or indicates susceptibility to a disease. For purposes of this application, biomarker encompasses both protein and mRNA.

As used herein, the term "mRNA" refers to messenger RNA or any fragment of a messenger RNA.

As used herein, the term "shRNA" refers to small hairpin RNA or short hairpin RNA. shRNA is a sequence of RNA that makes a tight hairpin turn that can be used to silence gene expression via RNA interference. For purposes of this application, CIP2A shRNA is used to silence CIP2A gene expression in HeLa cells. The CIP2A shRNA is obtained from a commercial source (Thermo Scientific Open Biosystems).

As used herein, the term "protein" refers to a chain of at least two amino acids. The terms "polypeptide," "peptide," or "protein" are used interchangeably.

As used herein, the term "primer" refers to a nucleotide sequence which can be extended by template-directed polymerization. For the purpose of this application, the term "nucleotide sequence" is intended to include DNA or modification thereof.

As used herein, the term "neoplasia" refers to the abnormal proliferation of cells, wherein the growth of the cells exceeds, and is uncoordinated with that of the normal tissues around it and may cause a lump or tumor.

As used herein, the term "chemical agent" refers to a substance used to extract nucleic acids (e.g., DNA or RNA) or proteins from a biological sample. Chemical agents used to extract nucleic acids include, but are not limited to, guanidinum thiocyanate, phenol-chloroform and the like. Chemical agents used to extract proteins include, but are not limited to, NP-40, SDS, Triton X-100, Tween-20, N-laurly sarcosine, olefine sulphates and the like.

As used herein, the term "AUC" refers to area under the curve.

As used herein, the term "ROC" refers to Receiver Operating Characteristics Analysis. ROC analysis is a standard statistical tool for evaluation of clinical tests. ROC assesses the performance of the system in terms of "Sensitivity" and "1—Specificity" for each observed value of the discriminator variable assumed as decision threshold (i.e., cutoff value to differentiate between two groups of response). For ELISA, the cutoff value can be shifted over a range of observed values (i.e., $OD_{450nm}$ reading), and Sensitivity and 1—Specificity can be established for each of these values. The optimal pair of Sensitivity and Specificity is the point with the greatest distance in a Northwest direction.

The present invention provides a novel biomarker for detection of cervical diseases. In particular, the present inventors discovered the use of CIP2A as a biomarker to detect and diagnose cervical cancer. Using clinical samples, the present inventors demonstrated that CIP2A increases its expression level in both mRNA and protein in cervical tissues derived from patients who suffer from cervical neoplasia. The increased expression level of CIP2A maintains throughout various cancer stages (i.e., stage I, stage II, and stage III of cervical cancer).

The present invention also provides the use of CIP2A and at least one additional biomarker for detection of cervical diseases. In particular, the present inventors discovered that CIP2A, when used in combination with Ki67, TOP2A, MCM2, MCM5 or $p16^{INK4a}$, can provide an improved diagnostic assay with a high sensitivity and specificity.

There has been a long-felt need for identifying novel biomarkers that would permit early detection and diagnosis of cervical diseases. To date, there exists a limited number of molecular biomarkers commercially available. One such exception includes $p16^{INK4a}$ detection assay and kit for detection of cervical cancer. $P16^{INK4a}$ is recommended to be used in conjunction with Pap test. However, $P16^{INK4a}$ expression level is already elevated in cervical dysplasia phases (e.g., CIN2, and CIN3). Not all patients who have high $p16^{INK4a}$ expression level would develop cervical cancer. Besides $p16^{INK4a}$, there are no reliable biomarkers with acceptable sensitivity and specificity. The present inventors cured the prior art deficiency and fulfilled the long-felt need in this medical area.

The present inventors surprisingly discovered CIP2A as a biomarker for detection of cervical diseases in human. CIP2A is a recently discovered protein that is shown to inhibit PP2A tumor suppressor activity in human malignancies (Junttila M R et al., *Cell* 130(1): 51-62, 2007). To the best of the present inventors' knowledge, CIP2A has been associated with only three (3) types of human malignancies; namely, (i) head and neck squamous cell carcinoma, (ii) colon cancer, and (iii) gastric cancer. The mechanism of action for CIP2A in neoplasia is unclear. CIP2A is shown to inhibit PP2A activity toward c-myc serine 62 (S62), and affect its proteolygic degradation.

The present invention represents the first report linking CIP2A with cervical diseases such as cervical cancer. The present invention provides a novel and non-obvious finding that CIP2A is a reliable and accurate molecular biomarker for detection of cervical cancer. The present finding is unexpected because the present assay employing CIP2A provides a high sensitivity and specificity (>90%). Contrary to one's expectation, c-myc as well as PP2A expression levels do not change in patients suffering from cervical diseases. The unique and specific increase in CIP2A (but not PP2A and c-myc) provides high sensitivity and specificity.

Collection and Preparation Biological Samples

Biological samples of the cervix in humans (including cells or tissues) can be conveniently collected by methods known in the art. Usually, a cervical tissue (or cells thereof) can be harvested by trained medical staffs or physicians, under sterile environment. Cervical tissues or cells may be taken, for example, by scrapes, smears, or swabs. Swabs may include but are not limited to, spatulas, brushes, or brooms. Other means include punch biopsy, endocervical curettage, conization, resection tumor samples, tissue samples prepared by endoscopic means, needle-biopsies of organs, and the like. After harvested from patients, biological samples may be immediately frozen (under liquid nitrogen) or put into a storage, or transportation solution to preserve sample integrity. Such solutions are known in the art and commercially available, for example, UTM-RT transport medium (Copan Diagnostic, Inc, Corona, Calif.), Multitrans Culture Collection and Transport System (Starplex Scientific, Ontario, CN), ThinPrep® Paptest Preservcyt® Solution (Cytyc Corp., Boxborough, Mass.) and the like.

A. Sample Preparation: Protein Extraction

After collection, samples are prepared prior to detection of biomarkers. Sample preparation includes isolation of protein or nucleic acids (e.g., mRNA). These isolation procedures involve separation of cellular protein or nucleic acids from insoluble components (e.g., cytoskeleton) and cellular membranes.

In one embodiment, cervical tissues or cells are treated with a lysis buffer solution prior to isolation of protein or nucleic acids. A lysis buffer solution is designed to lyze tissues, cells, lipids and other biomolecules potentially present in the raw tissue samples. Generally, a lysis buffer of the present invention may contain a chemical agent that includes one or more of the following ingredients: (i) chaotropic agents (e.g., urea, guanidine thiocyanide, or formamide); (ii) anionic detergents (e.g., SDS, N-lauryl sarcosine, sodium deoxycholate, olefine sulphates and sulphonates, alkyl isethionates, or sucrose esters); (iii) cationic detergents (e.g., cetyl trimethylammonium chloride); (iv) non-ionic detergents (e.g., Tween®-20, polyethylene glycol sorbitan monolaurate, nonidet P-40, Triton® X-100, NP-40, N-octyl-glucoside); (v) amphoteric detergents (e.g., CHAPS, 3-dode-cyl-dimethylammonio-propane-1-sulfonate, lauryldimethy-lamine oxide); or (vi) alkali hydroxides (e.g., sodium hydroxide or potassium hydroxide). Suitable liquids that can solubilize the cellular components of biological samples are regarded as a lysis buffer for purposes of this application.

In another embodiment, a lysis buffer may contain additional substances to enhance the properties of the solvent in a lysis buffer (e.g., prevent degradation of protein or nucleic acid components within the raw biological samples). Such components may include proteinase inhibitors, RNAse inhibitors, DNAse inhibitors, and the like. Proteinase inhibitors include but not limited to inhibitors against serine proteinases, cysteine proteinases, aspartic proteinases, metallic proteinases, acidic proteinases, alkaline proteinases or neutral proteinases. RNAse inhibitors include common commercially available inhibitors such as SUPERase.In™ (Ambion, Inc. Austin, Tx), RNAse Zap® (Ambion, Inc. Austin, Tx), Qiagen RNase inhibitor (Valencia, Calif.), and the like.

B. Sample Preparation: Nucleic Acid Extraction

Nucleic acids, such as mRNA, can be conveniently extracted from biological samples obtained from cervix (i.e., cervical tissues) using standard extraction methods that are known in the art. Standard extraction methods include the use of a chemical agent such as guanidinium thiocyanate, phenol-chloroform extraction, guanidine-based extraction, and the like. Commercial nucleic acid extraction kits may be employed. For example, RNeasy Fibrous Tissue Mini Kit from Qiagen (Valencia, Calif.) and RNAimage Kit from Gen-Hunter Corporation (USA).

Detection of Protein Expression Level

After protein extraction, expression level of various biomarkers (e.g., CIP2A, TOP2A, MCM2, MCM5, $p16^{INK4a}$, $p14^{ARF}$ or Ki67) in the biological samples can be determined using standard assays that are known in the art. These assays include but not limited to Western blot analysis, ELISA, radioimmunoassay, fluoroimmunoassay, immunohistochemistry assay, dot-blot assay, and the like. In a preferred embodiment, expression level of biomarkers may be detected by Western blot analysis. In another preferred embodiment, CIP2A protein expression may be determined by Western blot analysis.

Western Blot

After cellular proteins are extracted or isolated from the biological samples (e.g., cervical tissues), the cellular proteins are separated using SDS-PAGE gel electrophoresis. The conditions for SDS-PAGE gel electrophoresis can be conveniently optimized by one skilled in the art.

Protein biomarkers in the gels can then be transferred onto a surface such as nitrocellulose paper, nylon membrane, PVDF membrane and the like. The conditions for protein transfer after SDS-PAGE gel electrophoresis may be optimized by one skilled in the art. Preferably, a PVDF membrane is used.

To detect the biomarker proteins, a first antibody specific for the protein of interest (e.g., CIP2A, $p16^{INK4a}$, or $p14^{ARF}$ etc) is employed. Bound cellular proteins (e.g., 50-100 µg) on the membrane are incubated with a first antibody in a solution. An optimized first antibody concentration (e.g., 0.2-2 µg/mL) may be used. Incubation conditions may be optimized to maximize binding of the first antibody with the bound biomarker proteins. For example, 1 µg/mL of the first antibody is used and incubation time is 1-6 hours. Preferably, the incubation time is 2 hours. The first antibody may either be a monoclonal antibody or polyclonal antibody. Antibodies against the various protein biomarkers can be prepared using standard protocols or obtained from commercial sources. Techniques for preparing mouse monoclonal antibodies or goat or rabbit polyclonal antibodies (or fragments thereof) are well known in the art. Optionally, the membrane is incubated with a blocking solution before the incubation with the first antibody. The blocking solution may include agents that reduce non-specific binding of antibody. An exemplary blocking solution may include 5% skim milk in PBST (0.1% Tween-20).

After the incubation with the first antibody, the unbound antibody is removed by washing. An exemplary washing solution includes PBST. Protein biomarker-first antibody complex can be detected by incubation with a second antibody that is specific for the first antibody. The second antibody may be a monoclonal antibody or a polyclonal antibody (e.g., mouse, rabbit, or goat). The second antibody may carry a label which may be a directly detectable label or may be a component of a signal-generating system. Preferably, the second antibody is a goat anti-rabbit antibody or goat anti-mouse antibody that is labeled with a peroxidase. Such labeled antibodies and systems are well known in the art.

Direct detectable label or signal-generating systems are well known in the field of immunoassay. Labeling of a second antibody with a detectable label or a component of a signal-generating system may be carried out by techniques well known in the art. Examples of direct labels include radioactive labels, enzymes, fluorescent and chemiluminescent substances. Radioactive labels include $^{124}I$, $^{125}I$, $^{128}I$, $^{131}I$, and the like. A fluorescent label includes fluorescein, rhodamine, rhodamine derivatives, and the like. Chemiluminescent substances include ECL chemiluminescent.

ELISA

In another embodiment, detection and quantification of protein biomarkers (e.g., CIP2A, $p16^{INK4a}$, $p14^{ARF}$, TOP2A, MCM2, MCM5 or Ki67) is determined by ELISA.

In a typical ELISA, a first antibody is immobilized onto a solid surface. Immobilization of the first antibody may be performed on any inert support useful in immunological assays. Examples of inert support include sephadex beads, polyethylene plates, polypropylene plates, polystyrene plates, and the like. In one embodiment, the first antibody is immobilized by coating the antibody on a microtiter plate. In another embodiment, the microtiter plate is a microtest 96-well ELISA plate, such as those sold under the name Nunc Maxisorb or Immulon.

The first antibody is an antibody specific (to bind or to recognize) the protein biomarkers of interest. The first antibody may either be a monoclonal antibody, polyclonal antibody, or a fragment thereof. The first antibody may be acquired via commercial sources, or prepared by standard protocols well known in the art. A solid surface includes a 96-well plate.

Protein biomarkers present in a biological sample are captured by the immobilized first antibody. To do so, a protein extract from biological samples is incubated with the immobilized first antibody. Conditions for incubation can be optimized to maximize the formation of protein biomarker-first antibody complex. Preferably, an incubation time of 2-8 hours and a temperature of 25° C. may be used. Unbound first antibody is removed by washing.

To detect the formation of protein biomarker-first antibody complex, a second antibody is used. The second antibody may either be a monoclonal antibody or polyclonal antibody. Preferably, the second antibody is a polyclonal antibody, derived from goat or rabbit. Preparation of the second antibody is in accordance with established protocol or commercially available. Incubation of the second antibody can conveniently be optimized to maximize the binding. Preferably, an incubation time of 2-8 hours and a temperature of 25° C. may be used. Unbound second antibody is easily removed by washing. The second antibody is either directly labeled or conjugated with a signal-generating system.

The methods of detecting the presence of a directly labeled second antibody or a second antibody conjugated with a signal-generating system are well known to those of skill in the art. Suitable direct labels include moieties such as fluorophores, radioactive labels, and the like. Examples of radioactive labels include but not limited to $^{32}P$, $^{14}C$, $^{125}I$, $^{3}H$, and $^{131}I$. Examples of fluorophores include but not limited to fluorescein, rhodamine, and the like.

The second antibody may conveniently be conjugated to a signal-generating system such as an enzyme. Exemplary enzymes include horseradish peroxidase (HRP), alkaline phosphatase, and the like. The conjugation of an enzyme to the second antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147-166. Detection of the presence of second antibody can be achieved simply by adding a substrate to the enzyme. The methodology of such enzyme-substrate interaction is well within one skilled in the art's capability.

Detection of mRNA Expression Level

The present invention is directed to a discovery that specific protein biomarker is elevated during the pathogenesis of cervical cancer. In one embodiment, cervical cancer biomarkers increase their steady-state mRNA expression levels. Detection of mRNA expression levels for various biomarkers (e.g., CIP2A, $p16^{INK4a}$, $p14^{ARF}$, TOP2A, MCM2, MCM5 and Ki67) includes standard mRNA quantitation assays that are well-known in the art. These assays include but not limited to qRT-PCR, Northern blot analysis, RNase protection assay, and the like.

In one embodiment, the present invention provides the use of qRT-PCR to detect the expression level of cervical cancer biomarkers. qRT-PCR (quantative reverse transcription-polymerase chain reaction) is a sensitive technique for mRNA detection and quantitation. Compared to Northern blot analysis and RNase protection assay, qRT-PCR can be used to quantify mRNA levels from much smaller samples.

Real-time polymerase chain reaction, also called quantitative real time polymerase chain reaction (Q-PCR/qPCR/qRT-PCR), is used to amplify and simultaneously quantify a targeted DNA molecule. It enables both detection and quantification (as absolute number of copies or relative amount when normalized to DNA input or additional normalizing genes) of one or more specific sequences in a DNA sample. Currently at least four (4) different chemistries, TaqMan® (Applied Biosystems, Foster City, Calif.), Molecular Beacons, Scorpions® and SYBR® Green (Molecular Probes), are available for real-time PCR.

All of these chemistries allow detection of PCR products via the generation of a fluorescent signal. TaqMan probes, Molecular Beacons and Scorpions depend on Förster Resonance Energy Transfer (FRET) to generate the fluorescence signal via the coupling of a fluorogenic dye molecule and a quencher moiety to the same or different oligonucleotide substrates. SYBR Green is a fluorogenic dye that exhibits little fluorescence when in solution, but emits a strong fluorescent signal upon binding to double-stranded DNA.

Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

Real-time PCR, when combined with reverse transcription, can be used to quantify messenger RNA (mRNA) in cells or tissues. An initial step in the reverse transcription PCR amplification is the synthesis of a DNA copy (i.e., cDNA) of the region to be amplified. Reverse transcription can be carried out as a separate step, or in a homogeneous reverse transcription-polymerase chain reaction (RT-PCR), a modification of the polymerase chain reaction for amplifying RNA. Reverse transcriptases suitable for synthesizing a cDNA from the RNA template are well known.

Following the cDNA synthesis, methods suitable for PCR amplification of ribonucleic acids are known in the art (See, Romero and Rotbart in Diagostic Molecular Biology: Principles and Applications pp. 401-406). PCR reagents and protocols are also available from commercial vendors, such as Roche Molecular Systems. PCR can be performed using an automated process with a PCR machine.

Primer sets used in the present qRT-PCR reactions for various biomarkers may be prepared or obtained through commercial sources. For purposes of this application, the primer sets used in this invention include primers ordered from Abi (Assay ID, HS00405413_ml) (Foster City, Calif.). Table 1 lists the primers and probes used in the present qRT-PCR assays for the detection of various genes.

TABLE 1

Primers and Probes used in qRT-PCR Assay

| Target Gene Names | Target Gene Function | Abi pre-developed TaqMan assay ID (Catalog Numbers) |
|---|---|---|
| CIP2A | cancerous inhibitor PP2A binding protein | Hs00405413_m1 |
| p16 (CDKN2) | cyclin dependant kinase inhibitor | Hs00233365_m1 |
| Ki67 | Invovle in cell proliferation | Hs01032443_m1 |
| Myc | transcription factor | Hs00153408_m1 |
| TOP2A | topoisomerase 2A | Hs00172214_m1 |
| MCM2 | mini-chrosome maintance protein 2 | Hs01091564_m1 |
| MCM5 | mini-chrosome maintance protein 5 | Hs01052142_m1 |
| PPP2R1A | PP2A structural subunit, alpha isoform | Hs01026388_m1 |
| PPP2R4 | PP2A regulator subunit | Hs00603515_m1 |
| PPP2R5A | PP2A regulator subunit | Hs00196542_m1 |
| PPP2CA | PP2A catalytic subunit | Hs00427259_m1 |
| PPP2R1B | PP2A structural subunit, beta isoform | Hs00988483_m1 |
| PPP2R5C | PP2A catalytic subunit | Hs00604902_m1 |
| GAPDH | housekeeping gene | 4326317E |

The primers used in the PCR amplification preferably contain at least 15 nucleotides to 50 nucleotides in length. More preferably, the primers may contain 20 nucleotides to 30 nucleotides in length. One skilled in the art recognizes the optimization of the temperatures of the reaction mixture, number of cycles and number of extensions in the reaction. The amplified product (i.e., amplicons) can be identified by gel electrophoresis.

Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displayed in a graphical format through software developed for real-time analysis.

In addition to the forward primer and reverse primer (obtained via commercial sources), a single-stranded hybridization probe is also used. The hybridization probe may be a short oligonucleotide, usually 20-35 bp in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 bp long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein. Further information on PCR amplification and detection using a Rotor-Gene can conveniently be found on Corbett's website.

In another embodiment, suitable hybridization probes such as intercalating dye (e.g., Sybr-Green I) or molecular beacon probes can be used. Intercalating dyes can bind to the minor grove of DNA and yield fluorescence upon binding to double-strand DNA. Molecular beacon probes are based on a hairpin structure design with a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The range of the primer concentration can optimally be determined. The optimization involves performing a dilution series of the primer with a fixed amount of DNA template. The primer concentration may be between about 50 nM to 300 nM. An optimal primer concentration for a given reaction with a DNA template should result in a low Ct-(threshold concentration) value with a high increase in fluorescence (5 to 50 times) while the reaction without DNA template should give a high Ct-value.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, Tetrahedron Letts., 22 (20): 1859-1862 using an automated synthesizer, as described in Needham-VanDevanter, D. R., et al. 1984, Nucleic Acids Res., 12: 6159-6168. Purification of oligonucleotides can be performed, e.g., by either native acrylamide gel electrophoresis or by anion-exchange HPLC as described in Pearson, J. D. and Regnier, F. E., 1983, J. Chrom., 255: 137-149.

Comparison of Expression Levels of Various Cervical Cancer Biomarkers

Expression levels of various cervical cancer biomarkers of the present invention (i.e., CIP2A, Ki67, MCM2, MCM5, TOP2A, p16$^{INK4a}$, and p14$^{ARF}$) in a biological sample obtained from a patient (suspected with cervical diseases) may be compared to the expression levels of these cervical cancer biomarkers obtained from normal cervical tissues. Normal cervical tissues include cervical tissues obtained from healthy individuals or cervical tissues obtained from an adjacent area to the cancer regions within the cervix of the cervical cancer patients under examination. Comparison may be performed by employing protein concentrations of the cervical cancer biomarkers, or $\Delta\Delta C_t$ values from qRT-PCR of the cervical cancer biomarker genes.

In certain embodiments, the step of comparing the expression levels of cervical cancer biomarkers (e.g., CIP2A) present in a patient sample to an expression level of the same biomarker known to be present in a normal healthy body sample is embodied as employing a cut-off value or threshold value for the concentration of that particular biomarker.

Kits

The present invention provides a kit of manufacture, which may be used to perform detecting either a protein or mRNA for a specific cervical cancer biomarker. In one embodiment, an article of manufacture (i.e., kit) according to the present invention includes a set of antibodies (i.e., a first antibody and a second antibody) specific for a particular protein biomarker (e.g., CIP2A, Ki67, MCM2, MCM5, TOP2A, p16$^{INK4a}$ or p14$^{ARF}$). In another embodiment, the present kit contains a set of primers (i.e., a forward primer and a reverse primer) (directed to a region of the gene specific to a particular biomarker (i.e., CIP2A, Ki67, MCM2, MCM5, TOP2A, p16$^{INK4a}$ or p14$^{ARF}$) and optionally a hybridization probe (directed to the same gene, albeit a different region).

Kits provided herein may also include instructions, such as a package insert having instructions thereon, for using the reagents (e.g., antibodies or primers) to quantify the protein expression level of mRNA expression level of a particular cervical cancer biomarker in a biological sample. Such instructions may be for using the primer pairs and/or the hybridization probes to specifically detect mRNA of a specific gene (e.g., CIP2A) in a biological sample. In another, the instructions are directed to the use of antibodies (either monoclonal or polyclonal) that recognize and bind to specific cervical cancer biomarker.

In another embodiment, the kit further comprises reagents used in the preparation of the sample to be tested (e.g. lysis buffer). The kits of the invention also may further comprise one or more antibodies which specifically bind to one or more of the biomarkers Ki67, p16$^{INK4a}$, MCM2, MCM5 or TOP2A.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1

Expression of CIP2A Protein in Cell Lines

We examined expression of CIP2A protein in various cancer cell lines. Six (6) cervical cancer cell lines were used. CIP2A protein expression was monitored by a Western blot assay. The cervical cancer cell lines used include CaSki, HeLa, HTB-32, HTB-33, HTB-34, and HTB-35. Cancer cells were cultured at 37° C. prior to protein assay. Cell lysate proteins were isolated using modified RIPA buffer (details in Experimental Methods and Protocols). SDS-PAGE was used to separate cellular proteins and subsequently transferred onto PVDF membranes, followed by detection using anti-CIP2A monoclonal antibody (Santa Cruz Biotech., Inc. CA; SC-80662) in a Western blot assay. CIP2A protein has a molecular size of ~90 kDa. β-actin was used as a control in the assay.

As shown in FIG. 1A, all six (6) cervical cancer cell lines expressed CIP2A protein. Immortalized normal cervical cells (i.e., END1, Ect1, and VK2) and a colon fibroblast cell line (i.e., CCD112-CoN) were used as controls. CIP2A protein was found to be undetectable in CCD112-CoN, and Ect1; while VK2 and END1 were found to express CIP2A protein. Memory epithelial cells also do not express CIP2A protein (data not shown).

Figure 1B:
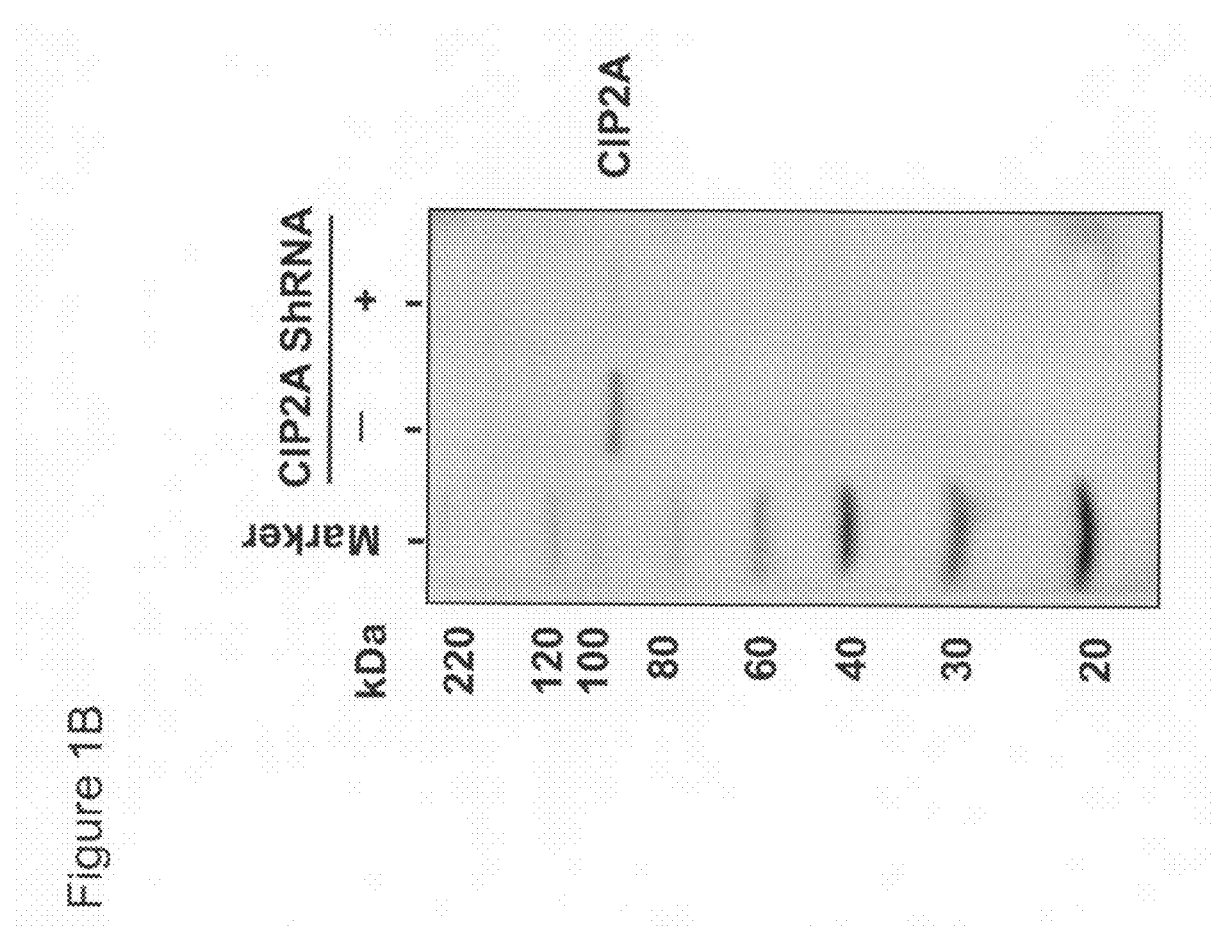
FIG. 1B depicts CIP2A protein expression in a HeLa cell line that has been treated with CIP2A shRNA. (−) lane indicates normal HeLa cell line; (+) lane indicates CIP2A shRNA knock down HeLa cell line.

To test the specificity of CIP2A monoclonal antibody, we used CIP2A shRNA knock down HeLa cells (Thermo Scientific Open Biosystems Expression Arrest GIPZ Lentiviral shRNAmir System, Catalog Number RHS4430-98912354), which specifically detected CIP2A protein as a single band as illustrated in FIG. 1B HeLa cell line (middle lane). The CIP2A detection was significantly reduced in CIP2A shRNA knockdown cell line (FIG. 1B, right lane).

In sum, these data indicate that CIP2A protein is abundantly expressed in multiple cervical cancer cell lines as well as in some normal cervical cell lines. CIP2A protein is not present in normal fibroblast cells. The amount of CIP2A protein expressed in different cervical cancer cells appears to vary, and there seems to lack a correlation between CIP2A protein expression and HPV infection.

Example 2

Expression of CIP2A Protein in Cervical Tissues From Patients

In this example, we studied CIP2A protein expression in cervical tissues obtained from patients. Snap-frozen cervical tissue specimens derived from both normal subjects and patients who suffered from cervical cancer diseases were purchased from tissue banks. Cervical tissues were homogenized using mechanical force under liquid nitrogen. Protein lysate was prepared using modified RIPA buffer. Western blot assay was used to examine CIP2A protein expression in these cervical tissue specimens.

Figure 2:
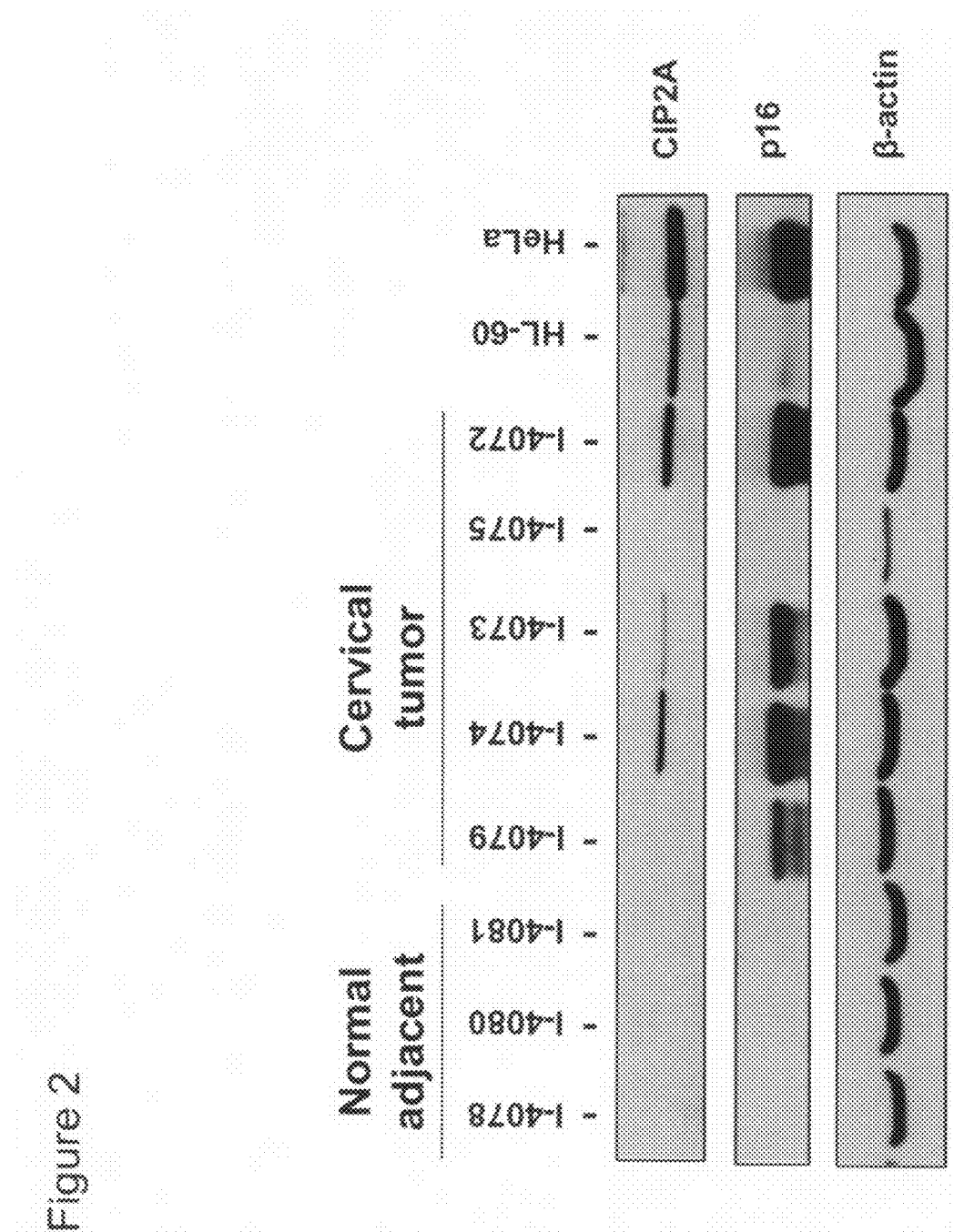
FIG. 2 depicts CIP2A protein expression in cervical tissues in a Western blot analysis. Note that CIP2A protein does not express in normal cervical tissues, but abundantly expressed in many cervical cancer tissues. HL-60 cells and HeLa cells served as controls.
Figure 3:
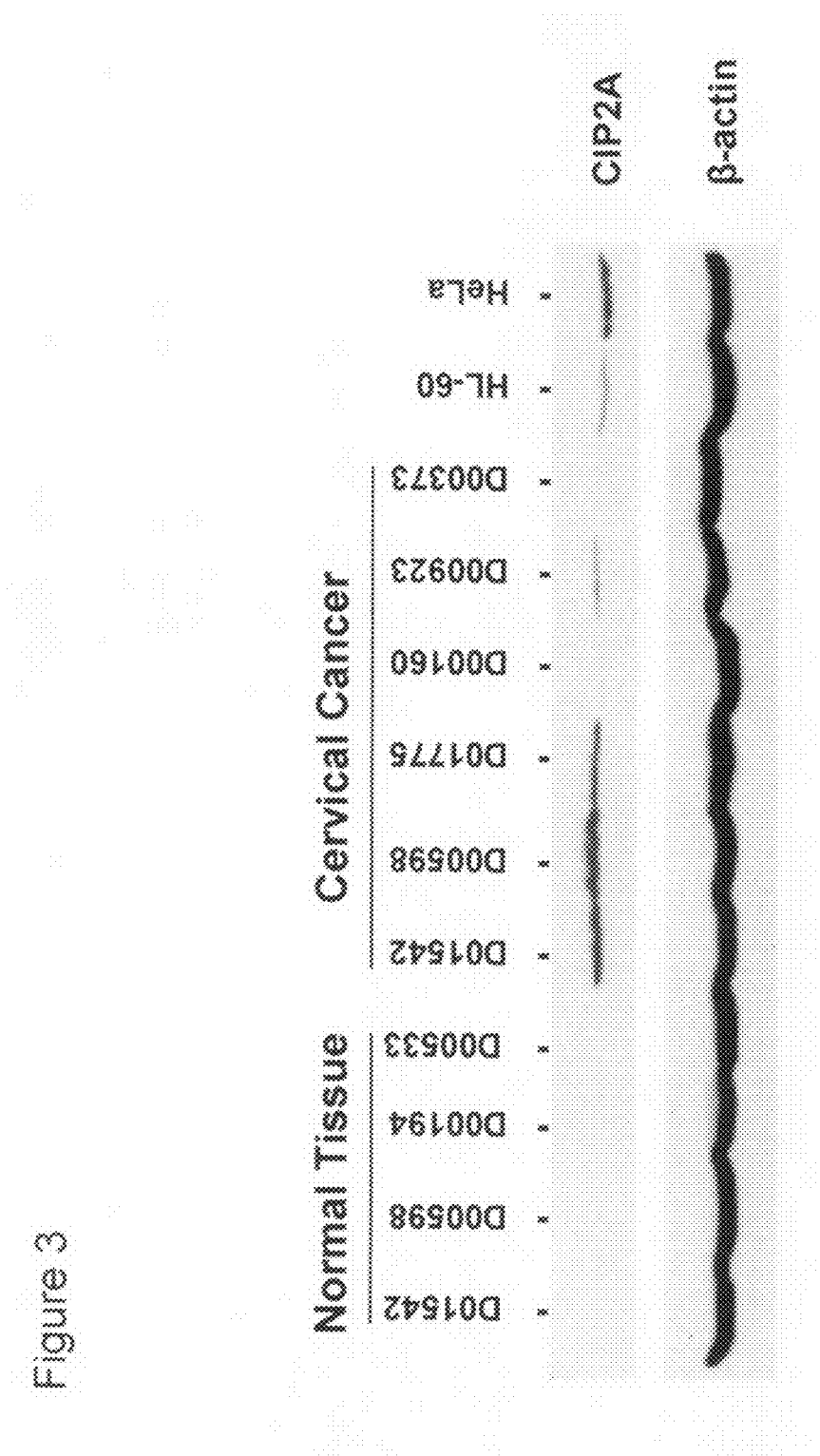
FIG. 3 further depicts CIP2A protein expression in additional cervical tissues in a Western blot analysis.

Cervical tissues from nine (9) normal subjects were found to have undetectable levels of CIP2A protein in our Western blot assay. (See, FIGS. 2 and 3). In contrast, out of the eleven (11) cervical tissues from cervical cancer patients, seven (7) were found to express CIP2A protein (i.e., ~64%). HL-60 and HeLa cell lysates were used in the assay as positive controls. (See, FIGS. 2 and 3).

In sum, these data show that CIP2A protein is expressed at high percentages in cervical tissues from patients who suffered cervical cancer diseases, whereas control cervical tissues do not express any CIP2A protein. Together, these data suggest that CIP2A is a reliable biomarker for cervical cancer.

Example 3

Expression of CIP2A mRNA in Cell Lines

Next, we examined CIP2A mRNA expression in various cancer cell lines. Steady-state mRNA levels were monitored using qRT-PCR. qRT-PCR was performed in a thermo-cycler. Data was analyzed by qPCR software MxPro-Mx3000P (Stratagene, La Jolla, Calif.). Total RNAs from various cancer cell lines were prepared using RNeasy Kit (Qiagen, Valencia, Calif.). RNA transcribed into cDNA using specific primers (Abi, HS00405413-ml) (Foster City, Calif.). qRT-PCR was performed using Stratagene (La Jolla, Calif.) and cDNA was synthesized under conditions specified (details see "Experimental Methods and Protocol").

Figure 4:
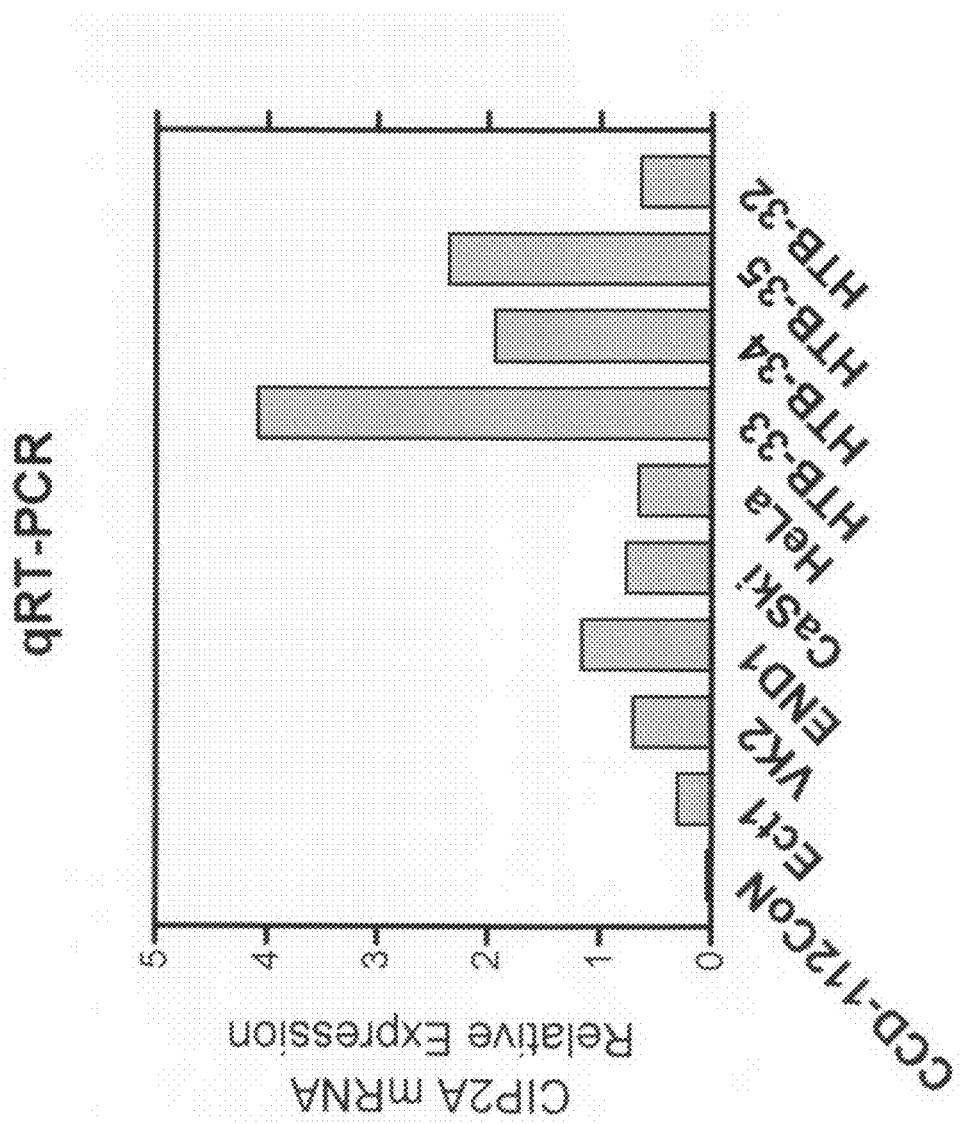
FIG. 4 depicts CIP2A mRNA relative expression in various cancer cell lines. The mRNA relative expression was determined using qRT-PCR (GAPDH as control).

Using CIP2A mRNA relative expression (i.e., quantified by a ΔΔCt method), we compared steady-state mRNA expression in various cervical cancer cell lines and compared them with those in normal cervical cell lines. Individual cell lines are depicted in the X-axis (of FIG. 4); and the relative expression of CIP2A mRNA is depicted in the Y-axis. As shown in FIG. 4, CIP2A mRNA expression is high in HTB-33, HTB-34, and HTB-35. Moderate CIP2A mRNA expression is observed in cervical cancer cell lines (i.e., CaSki, HeLa and HTB-32) as well as normal cervical cell lines (i.e., Ect1, VK2, END1). Normal colon fibroblast cell line (i.e., CCD-112CoN) exhibited only a minimal CIP2A mRNA expression.

In sum, CIP2A mRNA is abundantly expressed in many cervical cancer cell lines. It is not expressed in non-cervical cells such as fibroblast cells.

Example 4

Expression of CIP2A mRNA in Cervical Tissues From Patients

In this example, we studied CIP2A mRNA expression in cervical tissues obtained from patients. We obtained snap-frozen cervical tissue specimens from normal subjects and patients who suffered with cervical cancer. CIP2A mRNA was quantified in these cervical tissues using qRT-PCR as detailed in Example 3.

Figure 5A:
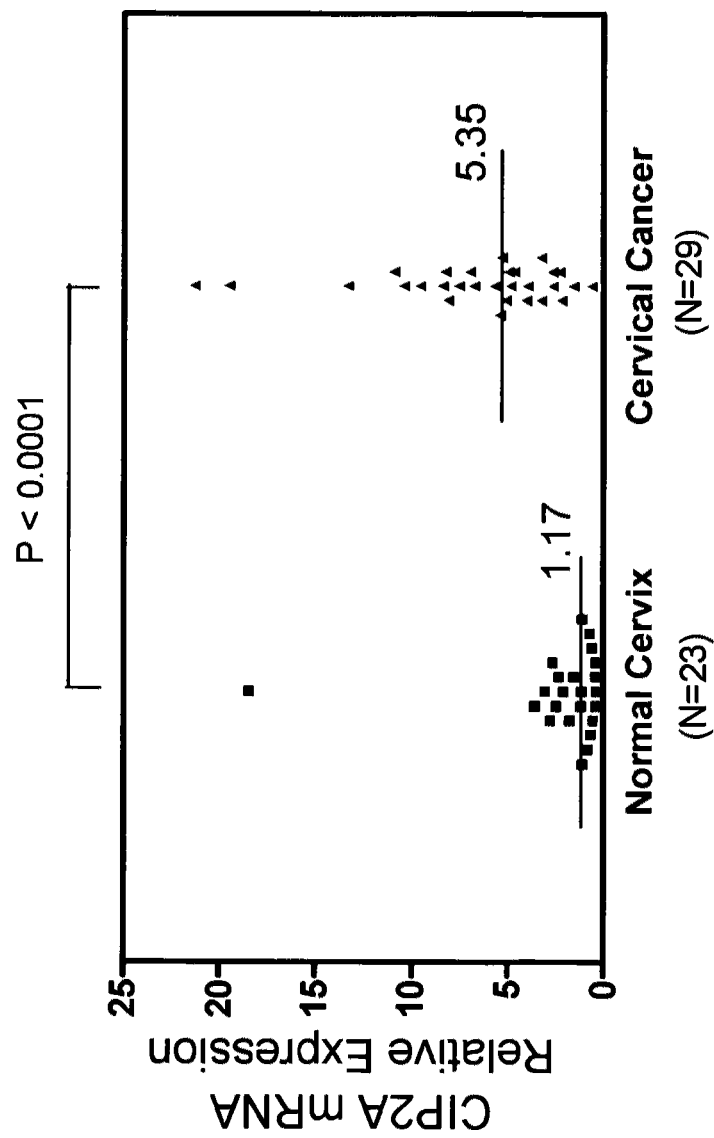
FIG. 5A depicts CIP2A mRNA relative expression in various cervical cancer tissues. Note that the CIP2A mRNA relative expression is higher in cervical cancer group (N=29) as compared to normal cervical group (N=23).
Figure 5B:
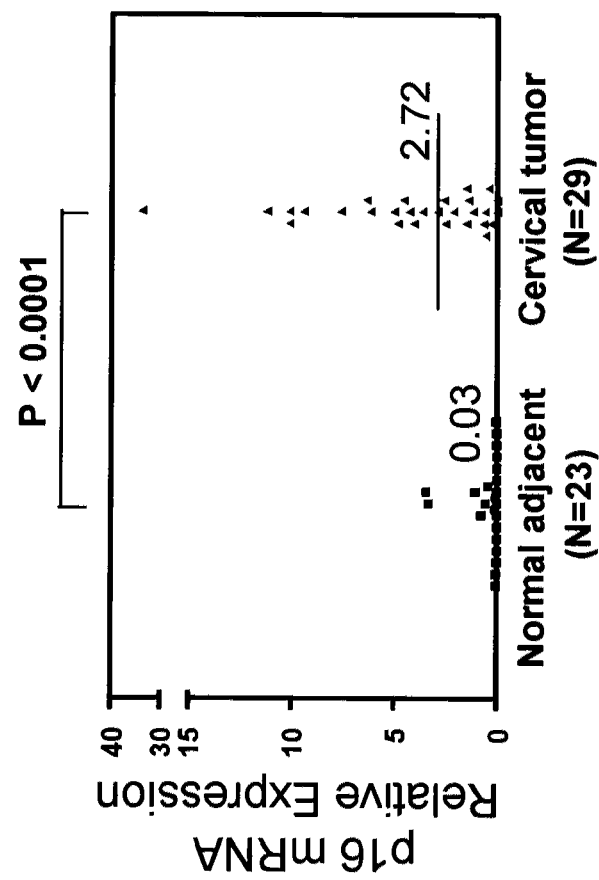
FIG. 5B depicts $p16^{INK4a}$ mRNA relative expression in various cervical cancer tissues. Note that the $p16^{INK4a}$ mRNA relative expression is higher in cervical cancer group (N=29) as compared to normal cervical group (N=23).

Cervical tissues from 23 normal subjects were found to have minimal levels of CIP2A mRNA expression in our qRT-PCR assay. (See, FIG. 5A). In contrast, 29 cervical tissues from cervical cancer patients express higher levels of CIP2A mRNA. The relative expression level of CIP2A in cervical cancer specimens varies from 0.6 to 21.3; the relative expression level of CIP2A in normal cervix specimen is between 0.4 and 3.7 (only one specimen is exceptional). Of interest is our finding that there appears a lack of clear correlation between CIP2A expression levels with HPV subtype, patient age (30-74), and patient race (African American, Caucasian, or Asian). The mRNA expression differences between these two groups are statistically significant ($p<0.0001$, Mann-Whitney Non-Parametric T-test) (See, FIG. 5A).

In contrast, when compared CYP21A mRNA expression level in 11 normal subjects and 16 cervical cancer patients, we found no statistical difference. Likewise, we found no statistical difference in the relative expression level of IRF4 mRNA in 17 cervical cancer patients.

Taken together, these data suggest that CIP2A mRNA is a reliable and specific biomarker for cervical cancer detection.

Example 5

Sensitivity And Specificity of CIP2A mRNA Detection Assay

Figure 6:
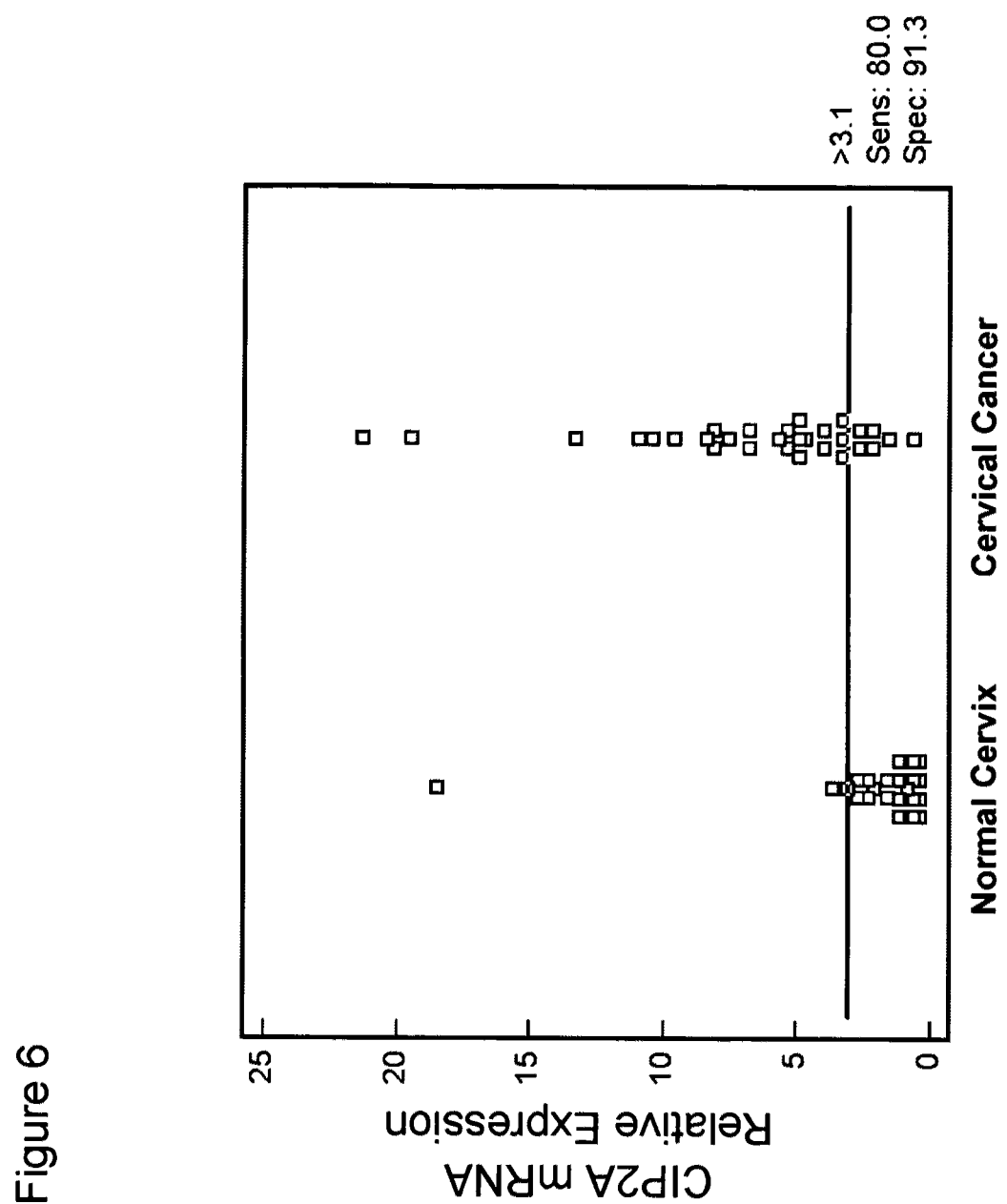
FIG. 6 depicts CIP2A mRNA relative expression with determination of sensitivity (80%) and specificity (91.3%) in normal and cervical cancer tissues.

We studied 29 patient samples and 23 control cervical tissues using qRT-PCR assay. Sensitivity and specificity of the CIP2A mRNA were calculated from these data. FIG. 6 summarizes the sensitivity and specificity results of the CIP2A mRNA detection assay. Statistical analysis was performed using MedCalc program interactive dot diagram.

Based on these results, our qRT-PCR mRNA assay has a sensitivity of at least 80% and a specificity of over 90%.

Example 6

ROC Analysis of CIP2A mRNA Detection Assay

Next, we conducted receiver operating characteristic (ROC) analysis to determine area under the curve (AUC). ROC plots were used to compare different experiments, even when the experiments might have different cutoff values (cut-off value is defined by value from negative control group). The calculated AUC allows one to evaluate the probabilities (1-specificity) and sensitivity. AUC is an important statistical feature of the ROC curves (i.e., for samples with sensitivity=specificity=100%, AUC would be 1.0) (See, FIG. 7).

Figure 7:
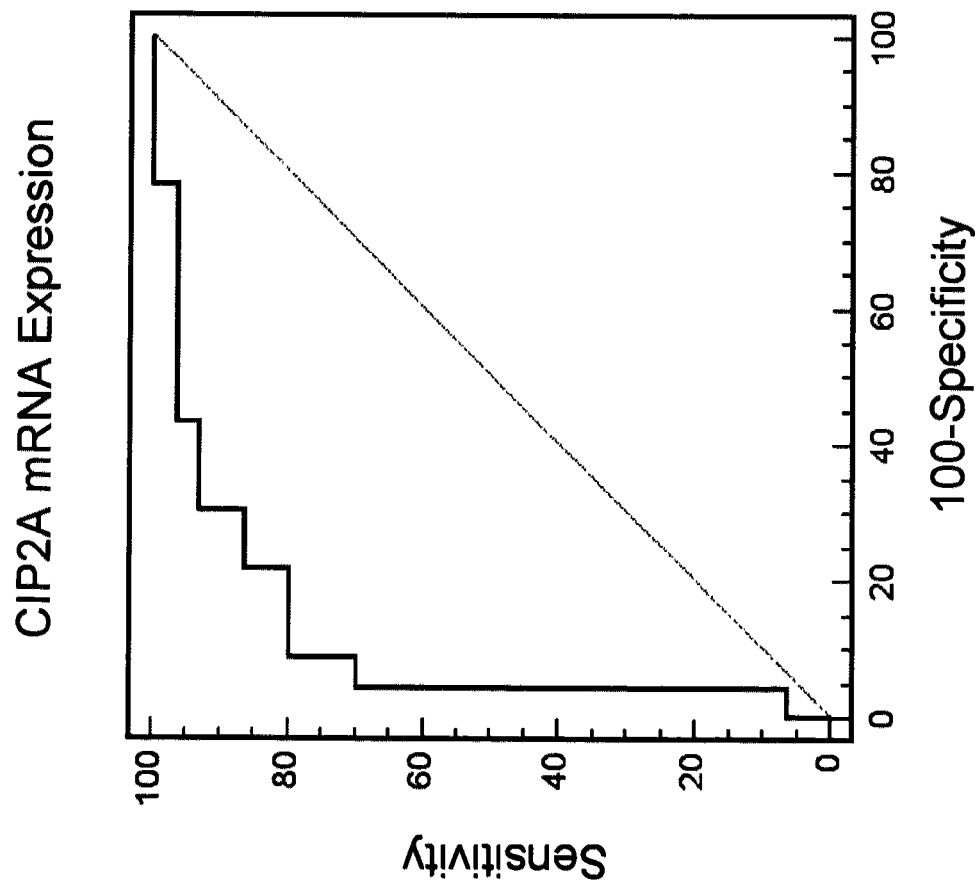
FIG. 7 depicts ROC analysis of CIP2A mRNA expression. The AUC value is 0.888.

ROC analysis of the CIP2A mRNA expression in normal and cervical cancer groups revealed an AUC of 0.888 (95% CI, 0.772 to 0.958, SE=0.0453) (See, FIG. 7). We observed CIP2A expression in cervical cancer patients but few in normal individuals. We concluded, based in this analysis, that CIP2A is a good biomarker for detection and diagnosis of cervical cancer in humans.

Example 7 Comparative Studies

CIP2A vs. p16$^{INK4a}$ mRNA Expression in Cervical Tissues

P16$^{INK4a}$ (MW~16 kDa) is a cyclin dependent kinase inhibitor involved in retinoblastoma pathway. P16$^{INK4a}$ expression is shown to correlate with development of cervical dysplasia and carcinoma. U.S. Pat. No. 6,709,832 discloses using p16$^{INK4a}$ as a diagnostic biomarker for cervical cancer detection. Mtm Laboratories has a commercial assay (i.e., Cervatech p16$^{INK4a}$ ELISA) to detect p16$^{INK4a}$ as a diagnostic tool for cervical cancer. The currently available p16$^{INK4a}$ commercial assay has a purported sensitivity of (~84-90%) and a specificity of (~76-87%) (Wentzensen et al., Cancer 107-9, 2006).

We compared the sensitivity and specificity between CIP2A and p16$^{INK4a}$ as biomarkers for cervical cancer detection diagnosis. Table 2 shows that CIP2A has a sensitivity of 80% and specificity of 91%, whereas p16$^{INK4a}$ has a sensitivity of 73% and a specificity of 91%. This data show that CIP2A mRNA assay is as good a biomarker for cervical cancer as p16$^{INK4a}$.

TABLE 2

Sensitivity and Specificity Comparative Studies

| | | Sensitivity | Specificity | PPV | NPV | AUC | P |
|---|---|---|---|---|---|---|---|
| mRNA | p16$^{INK4a}$ | 73% | 91% | 92% | 72% | 0.856 | 0.0001 |
| | CIP2A | 80% | 91% | 92% | 78% | 0.888 | 0.0001 |
| Protein | p16$^{INK4a}$ | 89% | 96% | 96% | 88% | — | — |
| | CIP2A | 83% | 100% | 100% | 80% | — | — |

PPV: positive predictive value
NPV: negative predictive value
AUC: area under curve
P: Statistical significance level of AUC (0.5) (ROC test)

Example 8

CIP2A Protein Expression in Matched-Pair Cervical Tissues

In this example, we evaluated tissue specificity of CIP2A expression. CIP2A protein expression in cancer tissues as well as their adjacent matched-pair normal tissues from the same individuals (who suffered cervical cancer) was compared. CIP2A protein expression was monitored using Western blot analysis as detailed above.

Figure 8:
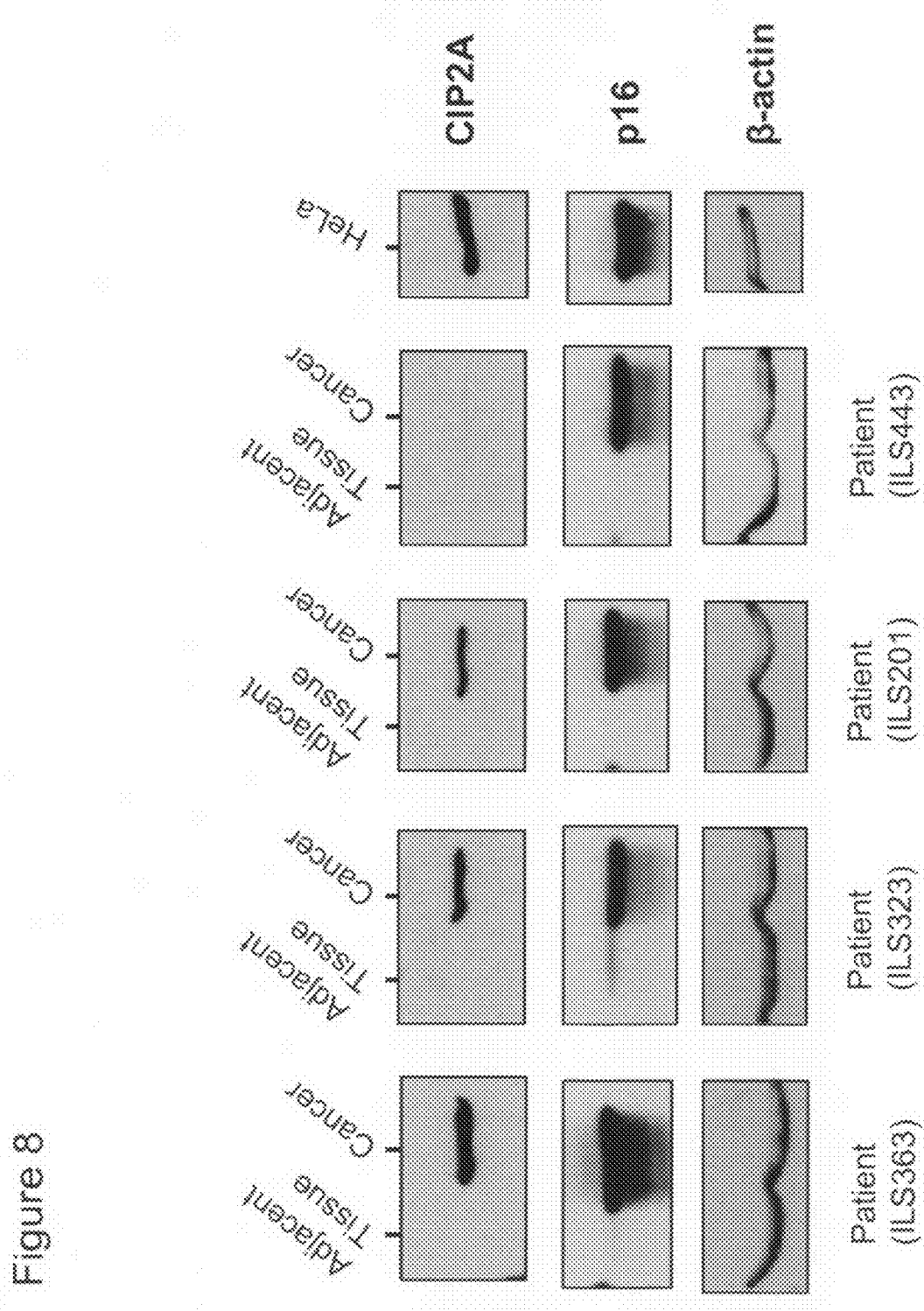
FIG. 8 depicts CIP2A protein expression in cervical tissues of four (4) patients (i.e., ILS363, ILS323, ILS201 and ILS443). Note that the CIP2A protein, like $p16^{INK4a}$, is abundantly expressed in three (3) patients, but not in ILS443 patient. Adjacent cervical tissues from the same individuals were used as controls for comparison purposes. HeLa cells also were used as a control. β-actin gene was used as a reference gene.

FIG. 8 depicts CIP2A protein expression in four (4) cervical cancer subjects (i.e., ILS363, ILS323, ILS201, and ILS443). Adjacent normal tissues (i.e., matched-paired) were collected about 1-4.5 cm distance away from the tumor tissue sites. HeLa cells were used as positive controls in this study.

As shown in FIG. 8, three (3) out of four (4) cervical cancer subjects expressed abundant levels of CIP2A protein in the tumor tissues (i.e., ILS363, ILS323, and ILS201) (See, FIG. 8). In contrast, the match-paired adjacent cervical tissues did not express CIP2A protein in these three (3) subjects. One of the cervical cancer subjects (i.e., ILS443) was found to express undetectable CIP2A protein in either tissue sites.

Altogether, these data support that CIP2A protein is specifically expressed in cervical cancer tissues, and not in normal cervical tissue, indicating tissue specificity.

Example 9

CIP2A mRNA Expression And Staging of Cervical Cancer

Development of cervical cancer is known to undergo different stages (namely, CIN1, CIN2, CIN3 (precancerous stages), followed by stage I, stage II, stage III and stage IV). These cancer stages are known well and in part characterized by ability of cancer cells to metastasize. We investigated CIP2A mRNA expression and their correlation with different cancer stages for cervical tissues. The goal of this study is to further assess the usefulness of using CIP2A as a biomarker for detection and diagnosis of cervical cancer in human subjects.

(i) CIP2A mRNA Expression Across Patient Population

The relative expression level of CIP2A mRNA increased across patient populations (52 patients) in cervical tissues taken from patients suffering from stage I, II and III cervical cancers in comparison the CIP2A mRNA levels in normal tissues from healthy individuals. The cervical tissues of 23 normal subjects, and 16 patients with stage I cervical cancer, 10 patients with stage II cervical cancer as well as 3 patients with stage III cervical cancer was compared for CIP2A mRNA levels. (See, FIG. 9). CIP2A mRNA levels were higher in cervical tissues from stage I, II and III cervical cancer patients in comparison to the level of CIP2A mRNA in normal tissue (FIG. 9).

Figure 9:
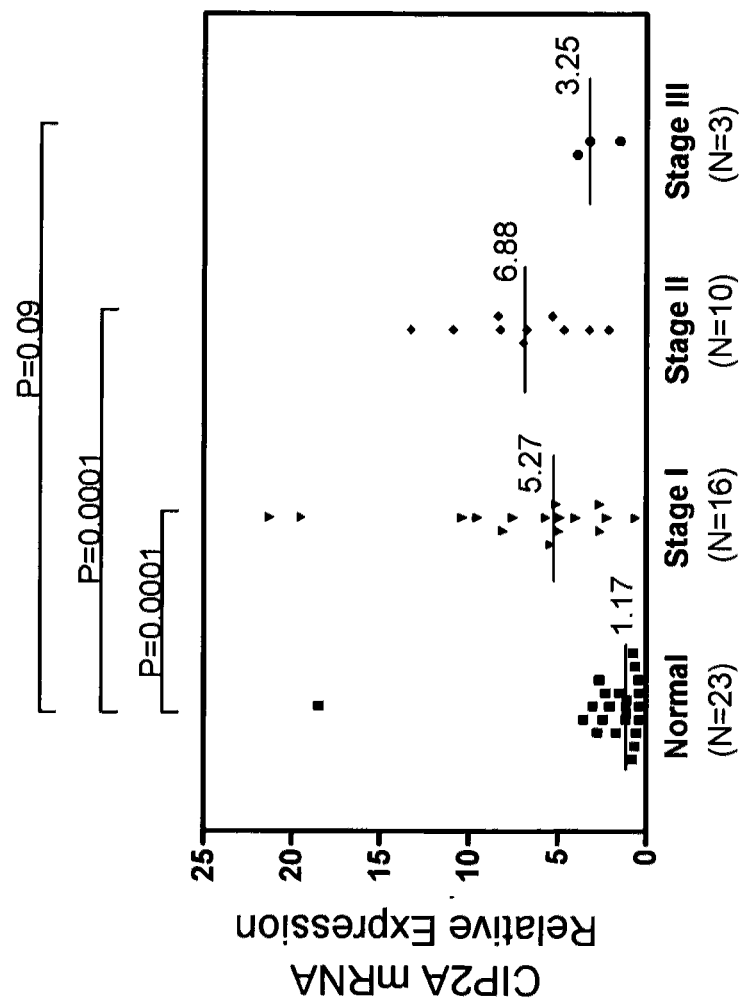
FIG. 9 depicts CIP2A mRNA relative expression in various cancer stages (i.e., stage I, stage II, and stage III). Note that CIP2A mRNA relative expression was increased in all three (3) cancer stages. CIP2A mRNA increases as early as stage I.

FIG. 9 summarizes the comparative results. The relative level of CIP2A mRNA expression in cervical tissues obtained from normal subjects (n=23) was 1.17. The relative level of CIP2A expression in cervical tissues from stage I cervical cancer patients (n=16) was 5.27; stage II cervical cancer patients (n=10) was 6.88; stage III cervical cancer patients (n=3) was 3.25 (FIG. 9). Relative expression is represented as $2^{-\Delta\Delta Ct}$. The relative levels of CIP2A mRNA expression in stages I, II and III cancer patients were statistically significantly higher than that in normal individuals. (non-parametric t-test, P values of 0.0001 for stage I; 0.0001 for stage II; and 0.09 for stage III) (See, FIG. 9).

In sum, our results show that CIP2A mRNA levels are elevated and can be detected in cervical tissues of patients suffering from stage I, stage II and stage III cervical cancer. These increased CIP2A expression can be detected in cervical tissues as early as stage I cervical cancer, thus providing an early biomarker for cervical cancer detection.

(ii) CIP2A mRNA Expression Within The Same Individual Patient

In order to avoid difference across various patients, CIP2A mRNA expression level was compared using adjacent non-cancerous (normal) cervical tissues from the same subject. The study involves determining the relative expression levels of CIP2A mRNA in both cancerous tissues and their adjacent match-paired normal tissues within the same single subject inflicted with cervical cancer.

A total of fourteen (14) cervical cancer patients were enrolled in this study, and their cervical tissues were collected from cancer sites and adjacent normal sites for measurement of CIP2A mRNA. Six (6) patients (i.e., ILS19363-D4, ILS11665-D4, ILS19323-D4, ILS19305-D4, ILS19205-D3, ILS19316-D1) were medically diagnosed as suffering from stage I cervical cancer. Five (5) patients (i.e., ILS19201-D4, ILS21298-D1, IND-00312-D5, IND-00306-D5, IND-00319-D4) were medically diagnosed as suffering from stage II cervical cancer. And three (3) patients (i.e., ILS-10443-D3, ILS11681-D2, ILS11681-X1) were medically diagnosed as suffering from stage III cervical cancer. Cervical tissues were collected and mRNA levels quantified as previously described in Example 3.

Figure 10:
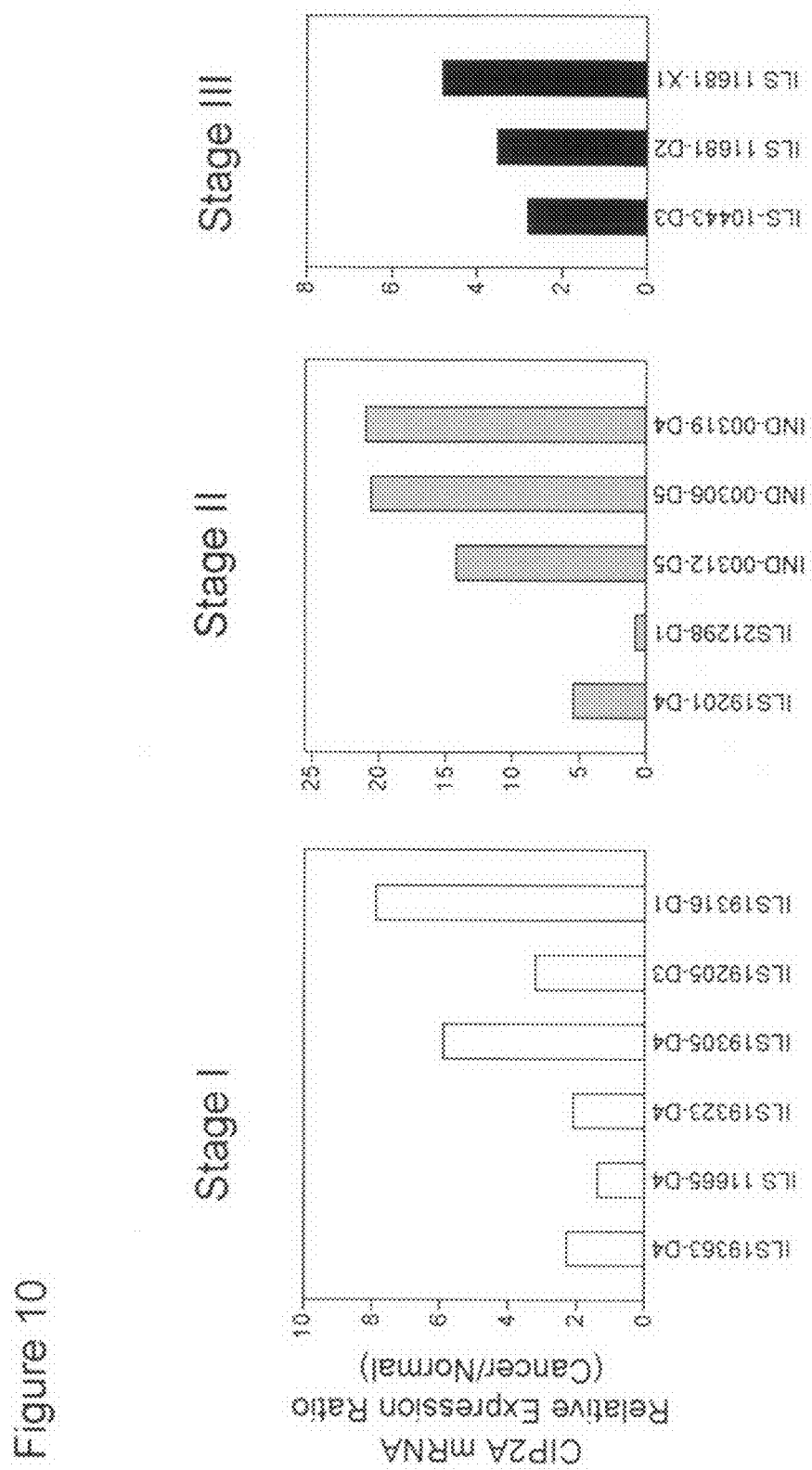
FIG. 10 depicts CIP2A mRNA relative expression ratio (cancer/normal) in various cervical tissues obtained from patients suffering from various stages of cervical cancer. The relative expression ratio was calculated using adjacent normal tissues from the same individual. Note that CIP2A mRNA relative expression ration was elevated in most cases.

In six (6) stage I cervical cancer patients, the relative expression ratio of CIP2A mRNA was at least 1.8:1. In five (5) stage II cervical cancer patients, the relative expression ratio of CIP2A exceeded 5:1 in four (4) of the five (5) patients, except one (1) patient (i.e., ILS21298-D1). In three (3) stage III cervical cancer patients, the relative expression ratio of CIP2A was at least 2.5:1. (See, FIG. 10). When compared to the same individuals using adjacent normal cervical tissues, we discovered CIP2A mRNA expression increased in almost all cervical cancer patients.

Because CIP2A mRNA expression (when compared to adjacent matched-pair normal tissues) increases in cervical cancer patients, these data indicate tissue specificity for employing CIP2A as a biomarker. Taken together, the clinical studies designed in this Example 9 suggest CIP2A is a reliable and sensitive biomarker for detection of cervical cancer.

Example 10

CIP2A Protein Expression And Staging of Cervical Cancer

We further examined CIP2A protein expression in patients inflicted with stages I, II and III cervical cancer and compared the CIP2A protein expression with cervical tissues obtained from healthy individuals. Table 3 summarizes the results of this study. In this study, we used an anti-CIP2A monoclonal antibody (SC-80662; Santa Cruz, Calif.) in a Western blot analysis to monitor CIP2A protein expression. Twenty-eight (28) non-cancer patient samples were examined, and all expressed undetectable expression levels of CIP2A protein.

CIP2A protein was found in twelve (12) out of sixteen (16) cervical tissues obtained from stage I abundantly expressed CIP2A protein. Nine (9) out of ten (10) stage II patients expressed CIP2A protein in cervical tissues. Two (2) out of four (4) stage III cervical cancer patients expressed CIP2A protein in cervical tissues. This finding is in accord with the hypothesis that CIP2A is involved in pathogenesis of cervical cancer and that CIP2A expression is a good biomarker for detection and diagnosis of cervical cancer.

TABLE 3

CIP2A Protein Expression in Cervical Tissues (Western Blot)

| Cervical Tissues | | | Protein Biomaker Expression (Western blot) | | | |
|---|---|---|---|---|---|---|
| Cervical Tissues | Cancer Status | Age | $p16^{INK4a}$ | CIP2A | c-myc | PPP2CA |
| Normal | Hysterectomy | 30 | – | – | H | L |
| Normal | Hysterectomy | 34 | – | – | H | L |
| Normal | Hysterectomy | 44 | – | – | H | L |
| Normal | Hysterectomy | 45 | – | – | H | L |
| Normal | Hysterectomy | 74 | – | – | H | L |
| Normal (Adjacent $_1$) | NA | 35 | – | – | L | L |
| Normal (Adjacent $_2$) | NA | 48 | – | – | L | L |
| Normal (Adjacent $_3$) | NA | 46 | + | – | L | L |
| Normal (Adjacent $_4$) | NA | 41 | – | – | L | L |
| Normal (Adjacent $_5$) | NA | 65 | – | – | L | L |
| Normal (Adjacent $_6$) | NA | 50 | – | – | L | L |
| Normal (Adjacent $_7$) | NA | 44 | – | – | L | L |
| Normal (Adjacent $_8$) | NA | 27 | – | – | H | H |
| Normal (Adjacent $_9$) | NA | 54 | – | – | H | H |
| Normal (Adjacent $_{10}$) | NA | 31 | – | – | H | H |
| Normal (Adjacent $_{11}$) | NA | Unknown | – | – | H | H |
| Normal (Adjacent $_{12}$) | NA | Unknown | – | – | L | H |

TABLE 3-continued

CIP2A Protein Expression in Cervical Tissues (Western Blot)

| Cervical Tissues | | | Protein Biomaker Expression (Western blot) | | | |
| --- | --- | --- | --- | --- | --- | --- |
| Cervical Tissues | Cancer Status | Age | p16$^{INK4a}$ | CIP2A | c-myc | PPP2CA |
| Normal (Adjacent $_{13}$) | NA | Unknown | – | – | H | H |
| Normal (Adjacent $_{14}$) | NA | 44 | – | – | H | L |
| Normal (Adjacent) | NA | 30 | – | – | H | H |
| Normal (Adjacent) | NA | 31 | – | – | L | H |
| Normal (Adjacent) | NA | 39 | – | – | H | L |
| Normal (Adjacent) | NA | 39 | – | – | H | L |
| Normal (Adjacent) | NA | 50 | – | – | H | L |
| Normal (Adjacent) | NA | 52 | – | – | NE | L |
| Normal (Adjacent) | NA | 53 | – | – | L | H |
| Normal (Adjacent) | NA | 53 | – | – | H | L |
| Normal (Adjacent) | NA | 59 | – | – | H | L |
| Cancer $_8$ | Stage I | 27 | + | – | L | H |
| Cancer $_{10}$ | Stage I | 31 | + | + | L | H |
| Cancer | Stage I | 34 | + | + | L | H |
| Cancer $_1$ | Stage I | 35 | + | + | H | H |
| Cancer | Stage I | 42 | + | – | L | L |
| Cancer | Stage I | 43 | + | + | L | H |
| Cancer | Stage I | 43 | + | + | L | H |
| Cancer $_3$ | Stage I | 46 | + | + | L | H |
| Cancer | Stage I | 48 | – | – | H | H |
| Cancer $_2$ | Stage I | 48 | – | – | H | L |
| Cancer | Stage I | 50 | + | + | L | H |
| Cancer | Stage I | 52 | + | + | L | H |
| Cancer | Stage I | 52 | + | + | L | H |
| Cancer $_9$ | Stage I | 54 | + | + | L | H |
| Cancer | Stage I | 76 | + | + | H | H |
| Cancer | Stage I | 79 | + | + | L | H |
| Cancer | Stage II | 28 | + | + | L | H |
| Cancer | Stage II | 39 | + | + | H | H |
| Cancer $_4$ | Stage II | 41 | + | + | H | H |
| Cancer | Stage II | 41 | + | + | L | H |
| Cancer | Stage II | 61 | + | + | H | H |
| Cancer $_5$ | Stage II | 65 | + | – | H | L |
| Cancer | Stage II | 69 | – | + | H | H |
| Cancer $_{13}$ | Stage II | Unknown | + | + | L | H |
| Cancer $_{11}$ | Stage II | Unknown | + | + | H | H |
| Cancer $_{12}$ | Stage II | Unknown | + | + | H | H |
| Cancer | Stage III | 44 | + | + | H | H |
| Cancer $_7$ | Stage III | 44 | + | – | H | L |
| Cancer $_{14}$ | Stage III | 44 | – | – | L | L |
| Cancer $_6$ | Stage III | 50 | + | + | L | H |

Legend:
–: Protein expression was not detected by Western blot (below detection limits <1 ng)
+: Protein expression was detected by Western blot
H: Protein expression was high
L: Protein expression was low
NA: Not applicable
NE: Not enough material To confirm antibody specificity, we also used four (4) other anti-CIP2A antibodies (i.e., two (2) monoclonal antibodies—SC-80660 (Santa Cruz, Calif.) and AB61863 (Abcam, Cambridge, Mass.)) and two (2) polyclonal rabbit antibodies (affinity purified using immobilized epitope)—A301-453A and A301-454A (Bethyl Lab., Montgomery, Tex.). We observed that all of these anti-CIP2A antibodies used in our study could efficiently detect CIP2A protein in our Western blot assay.

We conclude from these studies that CIP2A may serve as a biomarker for detection of squamous cell carcinoma (e.g., in cervical tissues). Because squamous cell carcinoma represents ~99% of cervical cancer population, we believe that CIP2A is a reliable and sensitive biomarker for detection of cervical cancer and its staging.

As stated above, our studies indicate that the sensitivity and specificity of CIP2A detection in cervical cancer patient is ~80% (24/30) and ~100% (28/28), respectively. These data strongly suggest that CIP2A is a good biomarker for cervical cancer detection and diagnosis.

Example 11

CIP2A/PP2A/c-myc Pathway

CIP2A is recognized to bind to PP2A before exerting biological effects on c-myc protein to dampen its degradation. Because c-myc protein is an oncogene protein, the CIP2A/PP2A/c-myc pathway is speculated to be involved in tumor development. Recently, CIP2A is reported to be involved in head/neck squamous cell carcinoma and gastric cancer. However, the role of PP2A/c-myc in this tumor genesis is unclear.

(i) PP2A Expression in Cervical Cancer

PP2A is a serine/threonine phosphatase, and it is a tumor suppressor. PP2A is reported to over-express in some tumors. In this study, we examined various PP2A subunit expression (both protein and mRNA) in cervical cancer. There are three (3) PP2A subunits: (a) catalytic subunit (includes two isoforms, e.g., PPP2CA), (b) structure subunit (includes two isoforms, e.g., PPP2R1A and PPP2R1B), and (c) regulatory subunit (includes >10 isoforms, e.g., PPP2R5A, PPP2R5C, and PPP2R4).

Figure 11:
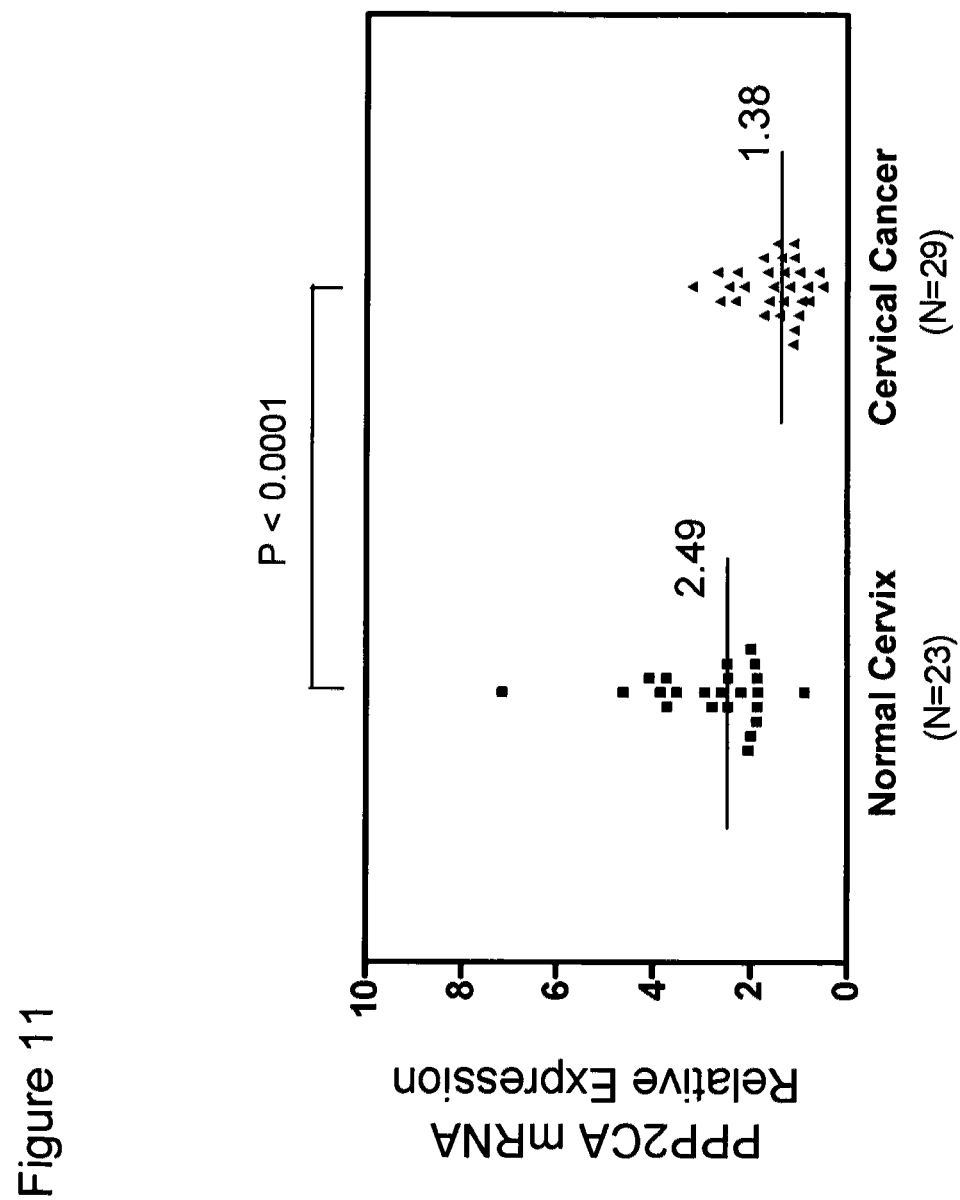
FIG. 11 depicts PPP2CA mRNA relative expression in normal cervical tissue (N=23) as compared to expression in cervical cancer tissues (N=29). The relative expression level of PPP2CA mRNA decreased in the cervical cancer tissue.
Figure 12:
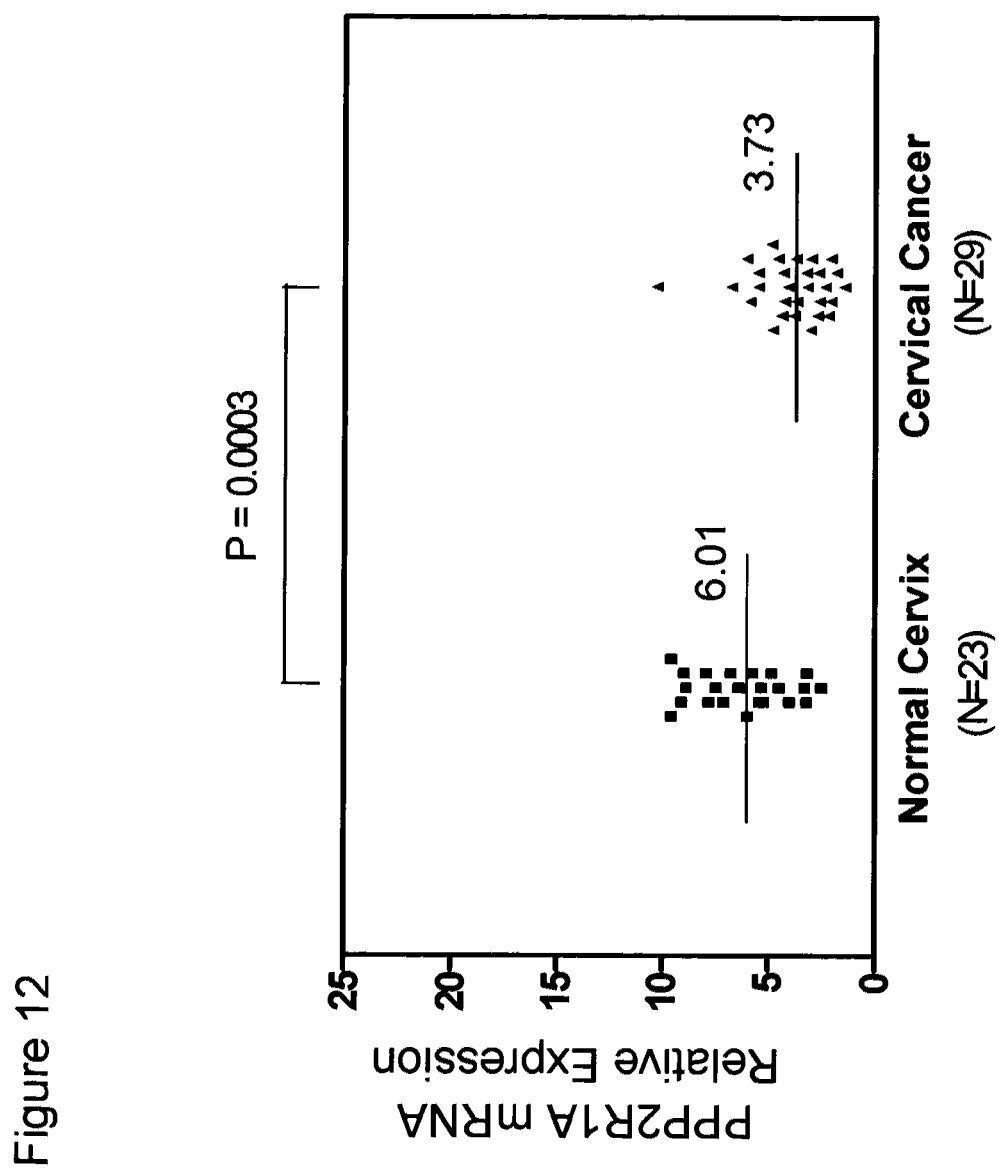
FIG. 12 depicts PPP2R1A mRNA relative expression in normal cervical tissue (N=23) as compared to expression in cervical cancer tissues (N=29). The relative expression level of PPP2R1A mRNA decreased in the cervical cancer tissue.
Figure 13:
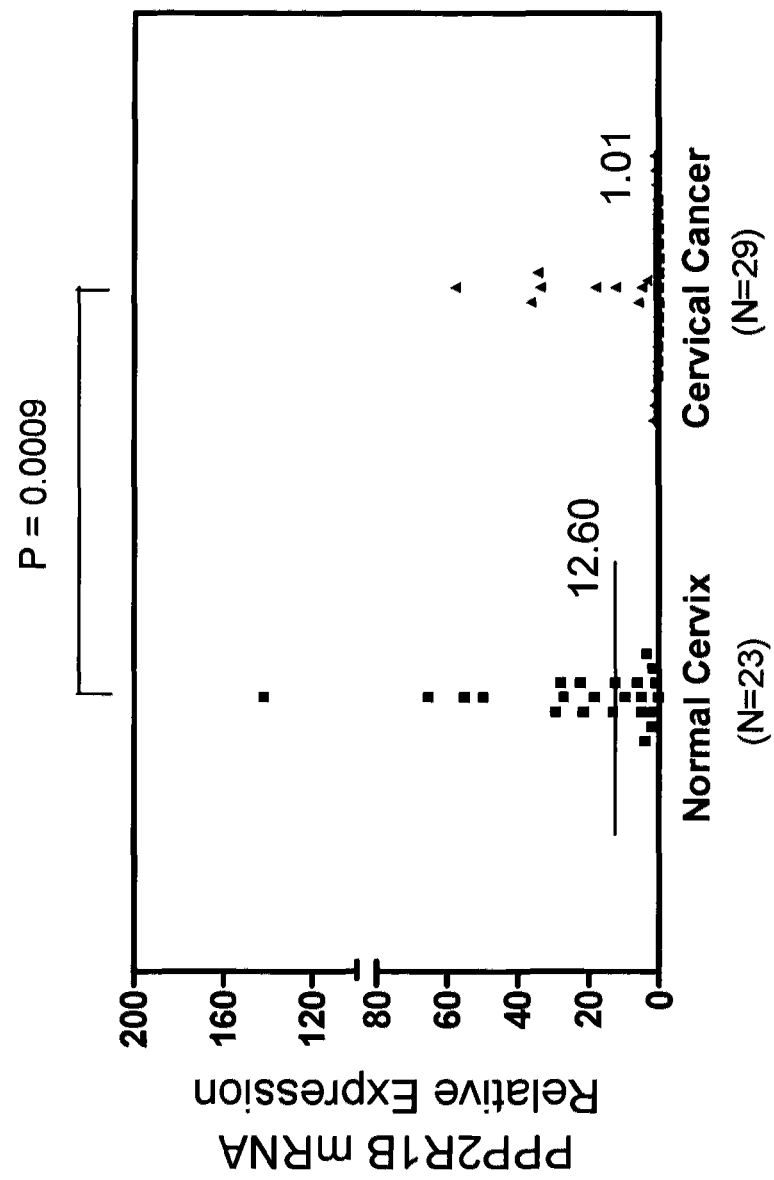
FIG. 13 depicts PPP2R1B mRNA relative expression in normal cervical tissue (N=23) as compared to expression in cervical cancer tissues (N=29). The relative expression level of PPP2R1B mRNA decreased in the cervical cancer tissue.
Figure 14:
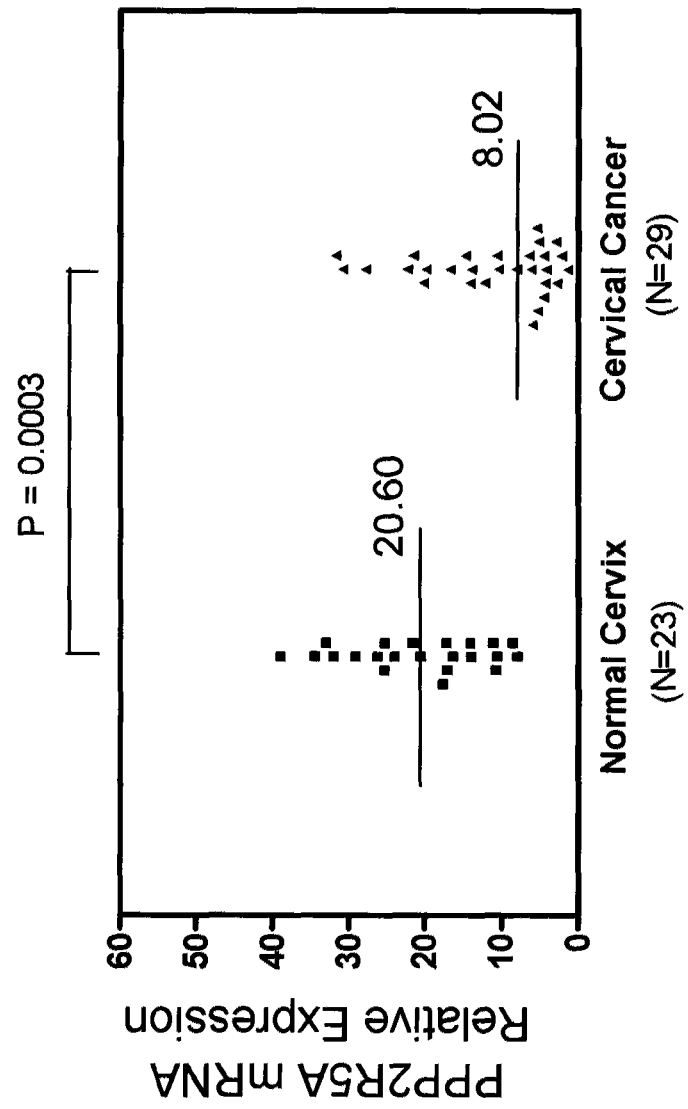
FIG. 14 depicts PPP2R5A mRNA relative expression in normal cervical tissue (N=23) as compared to expression in cervical cancer tissues (N=29). The relative expression level of PPP2R5A mRNA decreased in the cervical cancer tissue.
Figure 15:
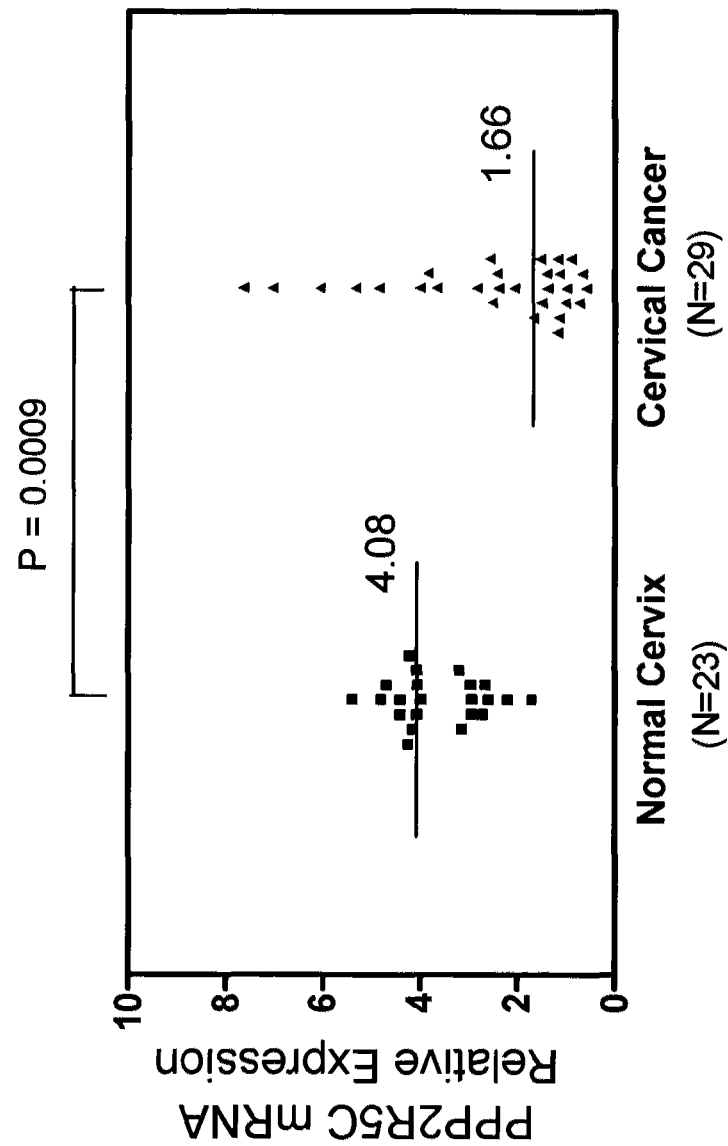
FIG. 15 depicts PPP2R5c mRNA relative expression in normal cervical tissue (N=23) as compared to expression in cervical cancer tissues (N=29). The relative expression level of PPP2R5A mRNA decreased in the cervical cancer tissue.
Figure 16:
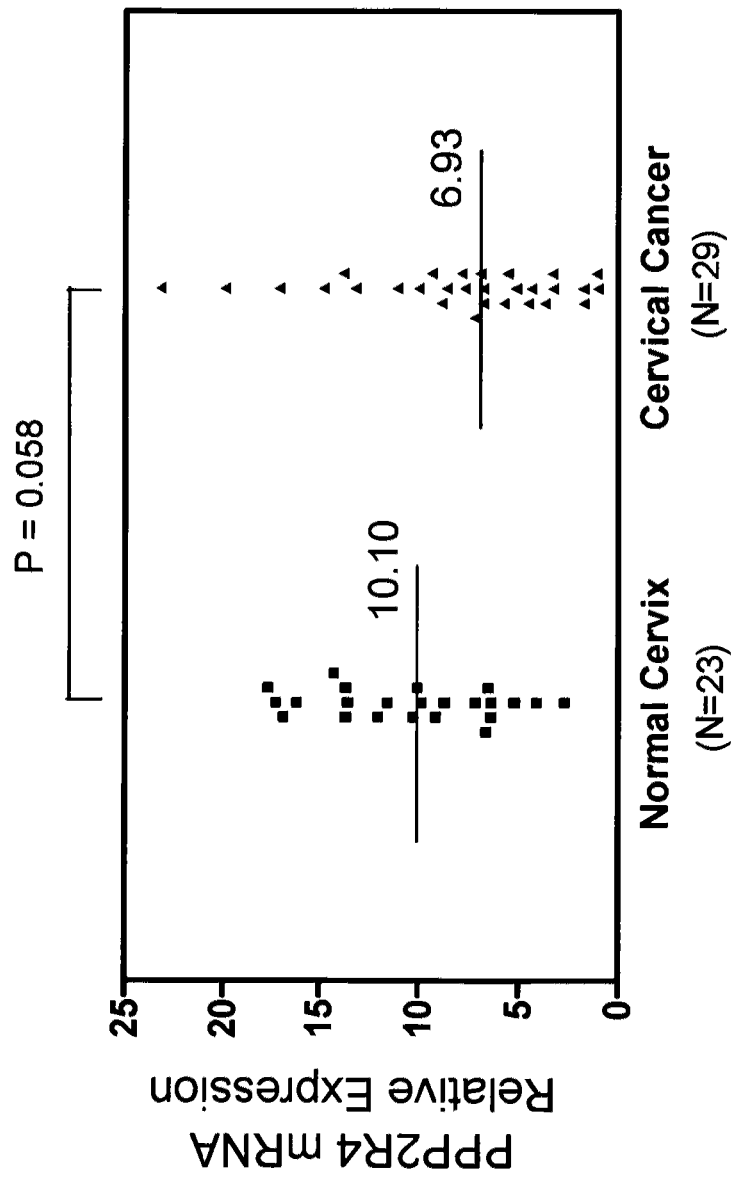
FIG. 16 depicts PPP2R4 mRNA relative expression in normal cervical tissue (N=23) as compared to expression in cervical cancer tissues (N=29). The relative expression level of PPP2R5A mRNA decreased in the cervical cancer tissue.

Surprisingly, we observed an increase in CIP2A expression in cervical cancer patients. We monitored mRNA expression for catalytic subunit (i.e., PPP2CA) and found that the mRNA decreased in the cervical cancer patients (See, FIG. 11). The mRNA expression in two (2) structural subunits (i.e., PPP2R1A and PPP2R1B) also decreased in the cervical cancer patients (See, FIGS. 12, and 13, respectively). The mRNA expression in three (3) regulatory subunits (i.e., PPP2R5A, PPP2R5C, and PPP2R4) also decreased in cervical patient tissues (See, FIGS. 14, 15 and 16, respectively).

In sum, our data show that mRNA expression of PP2A is down-regulated in cervical cancer patients. The mRNA behavior of PP2A is in sharp contrast to that of CIP2A (which mRNA level is increased), indicating specificity.

(ii) C-myc Expression in Cervical Cancer

C-myc is an oncogene expressed in some human cancers. The mechanism for aberrant expression of c-myc is complicate. In this study, we examined c-myc protein expression in cervical cancer. As shown above in Table 2, c-myc protein expression in cervical cancer tissues fails to exhibit a consistent and discernible pattern.

Figure 17:
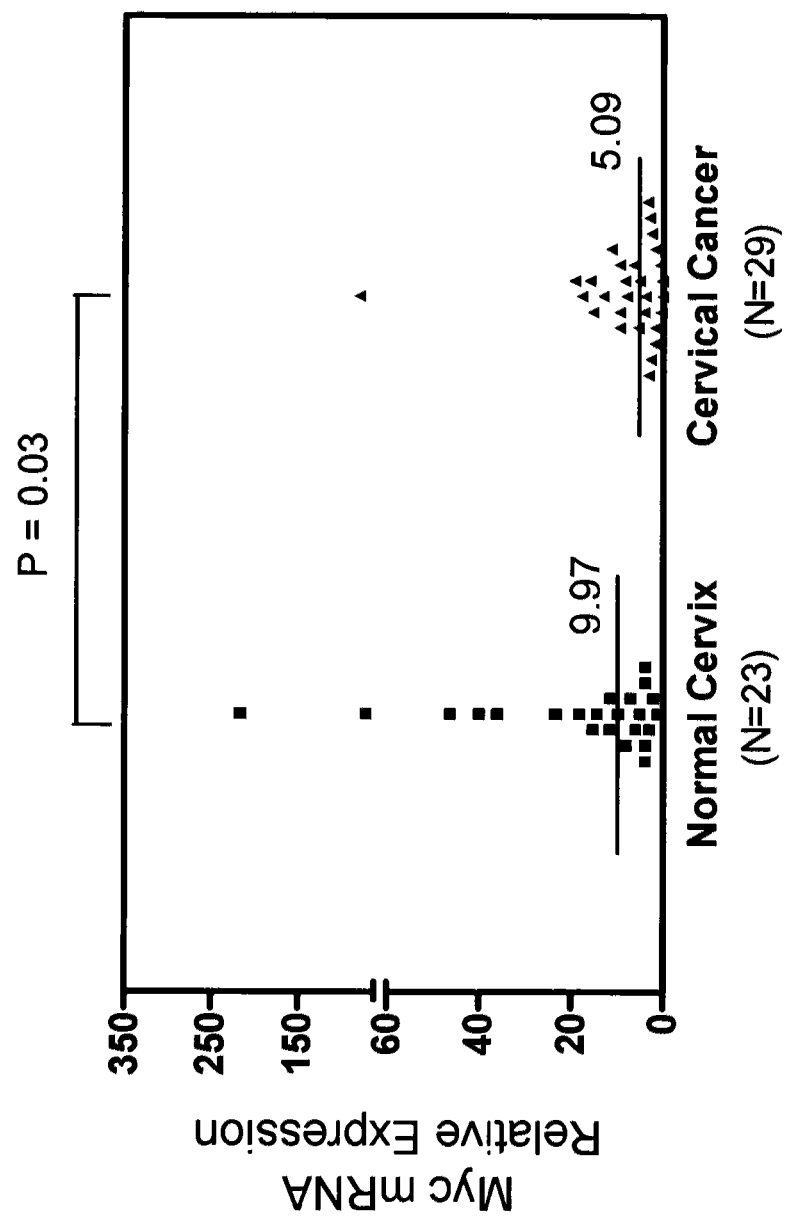
FIG. 17 depicts c-myc mRNA relative expression in normal cervical tissue (N=23) as compared to expression in cervical cancer tissues (N=29). The relative expression level of c-myc mRNA decreased in the cervical cancer tissue.

Next, we examined c-myc mRNA expression in cervical cancer patients. Contrary to CIP2A, the mRNA expression of c-myc slightly decreases (p=0.03) in cervical cancer tissues (See, FIG. 17). These data do not support c-myc as an optimal biomarker for cervical cancer detection and diagnosis.

Although CIP2A/PP2A/c-myc pathway may work together in the development of cervical cancer, our data strongly indicate that only CIP2A (but not PP2A or c-myc) is a good and reliable biomarker for detection of cervical cancer, indicating the high specificity of CIP2A as a biomarker.

Example 12

Single Biomarkers For Detection of Cervical Cancer

Figure 18:
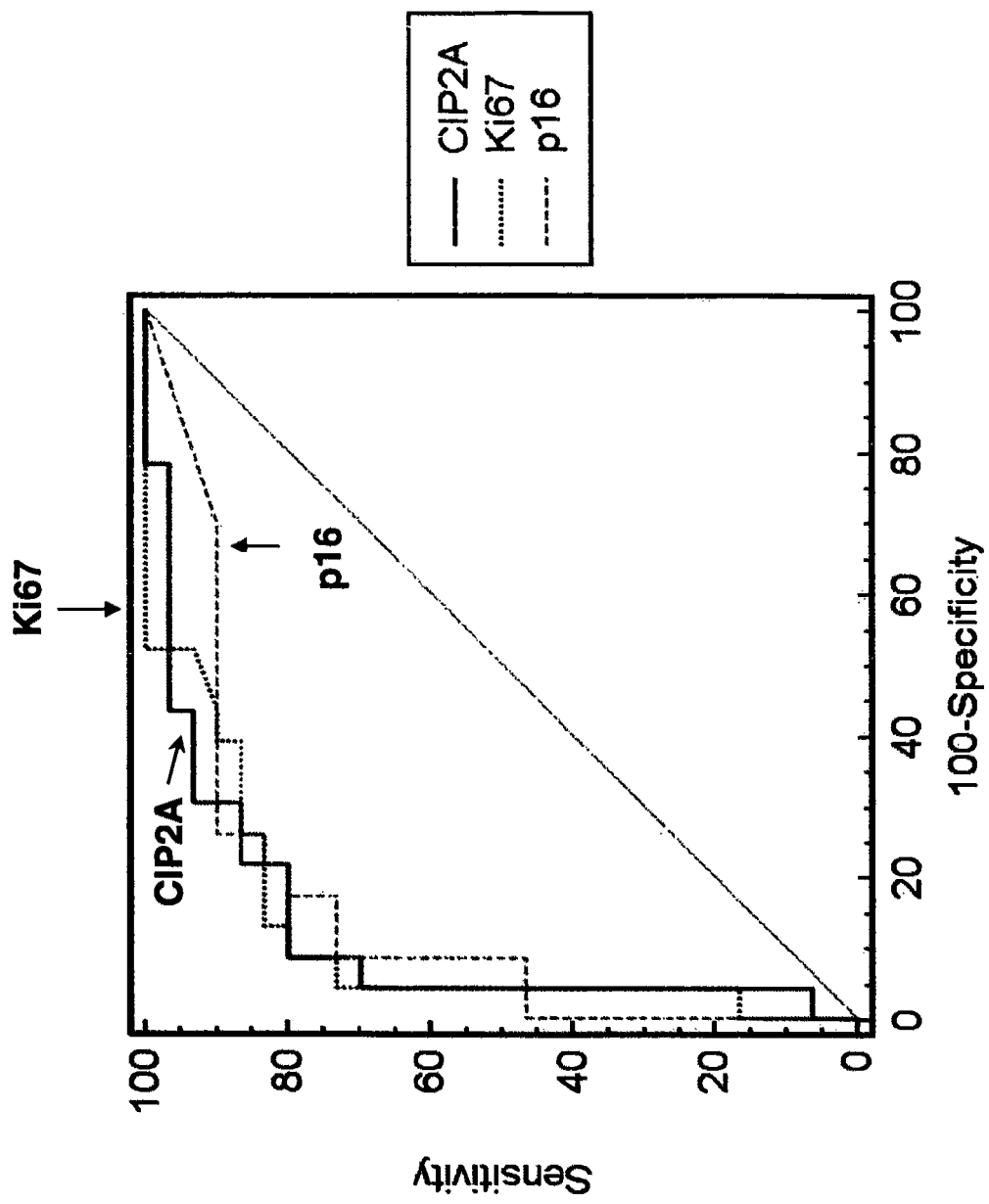
FIG. 18 depicts ROC analysis of CIP2A, Ki67, and $p16^{INK4a}$. Note that CIP2A has similar sensitivity and specificity as that of $p16^{INK4a}$.
Figure 19:
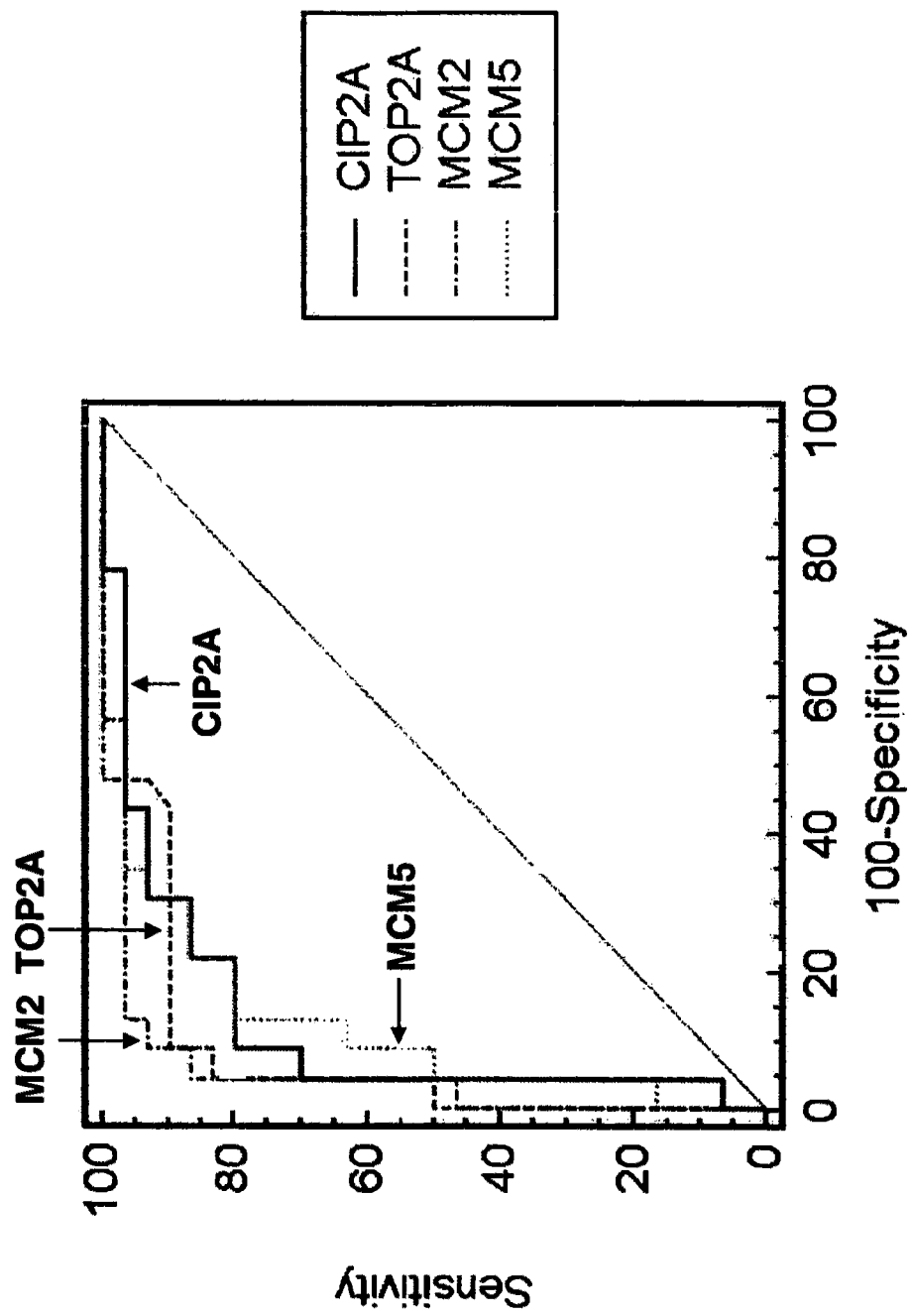
FIG. 19 depicts ROC analysis of CIP2A, TOP2A, MCM2, and MCM5.

In this study, we examiner six (6) biomarkers (used singly) in the detection of cervical cancer. These biomarkers include CIP2A, Ki67, TOP2A, MCM2, MCM5, and p16$^{INK4a}$. FIG. 18 summarizes the ROC analysis for CIP2A, Ki67 and p16$^{INK4a}$. FIG. 19 summarizes the ROC analysis for CIP2A, MCM2, MCM5, and TOP2A. All of the biomarkers examined (when used singly) exhibit similar AUC, indicating that these six (6) biomarkers share equivalent function in predicting or detecting cervical cancer.

Table 4 summarizes AUC values for all six (6) biomarker examined. All of these biomarkers have substantially the same AUC values, indicating equivalent functions shared by these biomarkers in cervical cancer detection.

TABLE 4

AUC Values for Various Biomarkers

| Biomarkers | AUC |
|---|---|
| CIP2A | 0.888 |
| Ki67 | 0.893 |
| TOP2A | 0.930 |
| MCM2 | 0.957 |
| MCM5 | 0.890 |
| p16$^{INK4a}$ | 0.856 |

Table 5 summarizes the sensitivity (%) and specificity (%) of individual biomarker.

TABLE 5

Sensitivity and Specifically of Individual Biomarkers

| Marker | Sensitivity | Specificity |
|---|---|---|
| CIP2A | 80% | 91% |
| Ki67 | 80% | 91% |
| TOP2A | 90% | 91% |
| MCM2 | 93% | 91% |
| MCM5 | 80% | 87% |
| p16$^{INK4a}$ | 73% | 91% |

Example 13

CIP2A in Combination With Other Biomarkers For Detection of Cervical Cancer

In this study, we examined the combined usage of at least two (2) biomarkers as a tool to detect or diagnose cervical cancer. As stated above, six (6) biomarkers were used (i.e., CIP2A, Ki67, TOP2A, MCM2, MCM5 and p16$^{INK4a}$ mRNA). In this series of study, we examined the combined use of two (2) biomarkers in pair. They include: (i) CIP2A+Ki67, (ii) CIP2A+TOP2A, (iii) CIP2A+MCM2, (iv) CIP2A+MCM5, and (v) CIP2A+p16$^{INK4a}$.

Table 6 summarizes the sensitivity (%) and specificity (%) of combined use of biomarkers.

TABLE 6

Sensitivity and Specifically of Combined Biomarkers

| Marker | Sensitivity | Specificity |
|---|---|---|
| CIP2A | 80% | 91% |
| CIP2A + Ki67 | 90% | 83% |
| CIP2A + TOP2A | 97% | 87% |
| CIP2A + MCM2 | 97% | 83% |
| CIP2A + MCM5 | 90% | 83% |
| CIP2A + p16$^{INK4a}$ | 90% | 83% |

Experimental Methods and Protocols

A. Cell Lines

Six (6) cancer cell lines (i.e., CaSki (CRL-11550), HeLa (CCL-2), HTB-32, HTB-33, HTB-34 and HTB-35) and two (2) non-cancer cell lines (i.e., HL-60 and MEG-01) were purchased from ATCC. Cancer cells were grown at 37° C. and 5% $CO_2$ in media as follows:

(1) CaSki (CRL-1550): modified RPMI 1640 medium (10 mM HEPES, 1 mM sodium pyruvate, 0.45% glucose, 0.15% sodium bicarbonate, 1% penicillin/streptomycin, and 1% glutamine) with 10% FBS;

(2) HeLa (CCL-2), HTB-34, and HTB-35: DMEM medium with 1% penicillin/streptomycin, 1% glutamine, and 10% FBS;

(3) HTB-32, HTB-33: McCoy's 5A medium with 1% penicillin/streptomycin, 1% glutamine, and 10% FBS;

(4) HL-60 and MEG-01: RPMI medium with 1% penicillin/streptomycin, 1% glutamine, and 10% FBS.

Cells were grown and split 1:5 to 1:10 every two to three days.

B. Protein Lysate Preparation from Cultured Cell Lines

Cancer cells were harvested and washed with PBS to remove serum, treated with 1.5 ml of 0.25% (w/v) trypsin and 0.53 mM EDTA dispersed, treated with 10 ml of ice-cold and collected by centrifugation (700 rpm, 8 minutes). Non-cancer cells were collected from cell culture by centrifugation (700 rpm, 8 minutes). All cells were washed once with 10 ml ice-cold PBS before use.

Cells were re-suspended, washed once more in 1 ml of cold PBS and spun down. After the PBS supernatant was removed, NP-40 cell lysis buffer (modified RIPA buffer containing 250 mM NaCl, 1% NP-40, 0.25% sodium deoxycholate, 50 mM Tris HCl buffer pH 8.0, 2 mM EDTA, and fresh protease inhibitor) was added, the cells were re-suspended and set on ice for 30 minutes.

Total cell lysate was collected by spinning for 10 minutes at 4° C. The protein concentration was determined by Protein Assay from Bio-Rad (Hercules, Calif.) based on the method of Bradford. Total protein lysate was stored in aliquots at ~80° C.

C. Total RNA Preparation from Cultured Cell Lines

RNA was obtained using RNeasy Mini Kit from Qiagen (Valencia, Calif.). Cells were grown and collected into a pellet as described previously. Cells were re-suspended in 350 µl Buffer RLT and passed through a QIAshredder spin column (Qiagen; Valencia, Calif.) and centrifuged for 2 min. 350 µl 70% ethanol was added to the lysate and mixed by pipetting. The mixture was centrifuged through an RNeasy spin column for 15 seconds at 8,000×g. The column was washed once with 700 µl Buffer RW1 and twice with 500 µl Buffer RPE. After the spin column was dried by centrifuge, RNA was eluted with 50 µl RNase-free water. The quality and quantity of RNA was determined by NanoDrop analysis. RNA was stored in aliquots at −80° C.

Cervical Tissues

A. Tissue Homogenization

Frozen tissue specimens were purchased from three commercial tissue banks: Ontario Tumor Bank; Folio BioSciences; and ILSbio, LLC. Tissue was disrupted and homogenized in liquid nitrogen using a mortar and pestle. The tissue was kept frozen in the whole process and homogenized tissue was stored in −80° C. for further analysis. For frozen tissue section for RNA preparation, it was cut into cubes (each dimension≤5 cm) and soaked overnight in RNAlater-ICE at −20° C. to minimizing RNA degradation.

B. RNA Preparation from Cervical Tissues

RNA from cervical tissue was obtained using RNeasy Fibrous Tissue Mini Kit from Qiagen (Valencia, Calif.). Homogenized tissue powder (≤30 mg) was added to and mixed with 300 µl Buffer RLT, 590 µl RNase-free water and 10 µl proteinase K solution. The mixture was incubated at 55° C. for 10 minutes then spun down at 20-25° C. for 3 minutes at 10,000 g. The supernatant was transferred into a new micro-centrifuge tube and mixed with 450 µl 100% ethanol. The mixture was passed through an RNeasy Mini spin column at room temperature and spun for 15 seconds at 8,000 g. The column was washed with 350 µl Buffer RW1, incubated with DNase I for 15 minutes and washed again with RW1. After washing with 500 µl Buffer RPE, the RNA was eluted from column with 50 µl RNase-free water. The quality and quantity of RNA was assessed by NanoDrop analysis. The RNA was stored in aliquots at −80° C.

C. DNA Preparation from Cervical Tissues

DNA was purified from tissue using Qiagen QIAamp DNA Mini Kit (Valencia, Calif.). Homogenized tissue powder (≤25 mg) was added to 100 µl Buffer ATL, mixed with 20 µl proteinase K, and incubated at 56° C. for 4-6 hours. Then, 200 µl Buffer AL was added and the sample incubated at 70° C. for 10 minutes. Then, 200 µl ethanol was added and the sample mixed by pulse-vortexing. The final mixture was passed by centrifuge through QIAamp Mini spin column at 6,000 g for 1 minute to allow DNA bind to column. The column was washed with 500 µl Buffer AW1 and 500 µl Buffer AW2 sequentially. DNA was eluted from the column with 2×200 µl Buffer AE and placed at −20° C. for long term storage. Yields and purity of DNA was determined with NanoDrop.

D. Preparation of Protein Lysate from Cervical Tissues

Homogenized cervical tissue powders were soaked in NP-40 cell lysis buffer for 60-120 minutes on ice to complete the lysis process. The NP-40 cell lysis buffer is modified RIPA buffer, which contains 250 mM NaCl, 1% NP-40, 0.25% sodium deoxycholate, 50 mM Tris HCl buffer pH 8.0, 2 mM EDTA, and fresh protease inhibitor. The total cell lysate supernatant was collected by spin for 30 minutes at 4° C. Protein concentration was determined by Bio-Rad (Hercules, Calif.). Protein Assay based on the method of Bradford. The total protein lysate was stored in aliquots at −80° C.

III. Analysis and Quantitation of mRNA mRNA expression was evaluated using qRT-PCR. For each sample, one-half micro-gram of total RNA, prepared as previously described, was reverse transcribed into cDNA using Superscript III (Invitrogen Life Technologies (Carlsband, Calif.)).

A mixture containing 0.5 mg total RNA, 1 µl oligo dT primer (50 µM), 1 µl Annealing Buffer, and RNase/DNase free water to a final volume of 8 µl was prepared. This mixture was incubated at 65° C. for 5 minutes, and then immediately placed on ice for at least 1 minute. 10 µl of 2× first-strand reaction mix and 2 µl of SuperScript III/RNase OUT Enzyme Mix was added to the reaction and the reaction incubated at 50° C. for 50 minutes. The reaction was terminated by incubating at 85° C. for 5 minutes.

The qRT-PCR was performed using Stratagene (La Jolla, Calif.) Fast Real-Time PCR System with validated primer sets. All primers were purchased from Applied Biosystems (Foster City, Calif.). Thermal cycler parameters were as follows: Heated to 95° C. for 3 minutes; 40 amplification cycles at 95° C. for 30 seconds (denaturing), 60° C. for 1 minute (annealing and extension). The amount of product in a particular sample was determined by interpolation from a standard curve of cycle threshold (Ct) values generated from dilution series with known amounts of gene product. Each gene is expressed as a relative ratio of gene to the housekeeping gene GAPDH. HeLa cell was used as calibrator for the analysis. The expression level of a gene was also represented as fold increase ($2^{-\Delta\Delta Ct}$), where $\Delta\Delta Ct=[\Delta\Delta Ct_{(cervical\ cancer)}]-[\Delta Ct_{(normal)}]$ and $\Delta Ct=[Ct_{(sample)}]-[Ct_{(GAPDH)}]$. All PCR assays were performed in triplicate. Results are representative average of two reactions.

IV. Western Blot Assay

For Western blot analysis, 50-100 μg total protein or 10-20 μg nuclear protein was separated by SDS-PAGE under reducing conditions and transferred to PVDF membranes. Membranes were blocked with 5% skim milk in PBST (0.1% Tween-20) for 1-2 hr at room temperature. Membranes were then incubated with diluted primary antibody for 120 min and then washed five times with PBST buffer. Membranes were incubated with peroxidase-labeled secondary antibody for 90 minutes at room temperature. Goat anti-rabbit IgG diluted 1:5,000 in PBST was used for assays employing a polyclonal primary antibody. Goat anti-mouse IgG (KPL, Gaithersburg, Md.) diluted 1:5,000 in PBST was used for assays employing a monoclonal primary antibody. All membranes were visualized using ECL chemiluminescence detection and film exposure.

V. Statistical Analysis

Mann-Whitney Non-parametric two-tailed T-test in Prism Graph Software was used to statistically analyze data for P value, mean, and median values. MedCalc software was used for ROC curve analysis, ROC curve comparison, and Interactive dot diagram for optimal cutoff, sensitivity, and specificity calculation.

All publications and patents cited in this specification are herein incorporated by reference in their entirety. Although the invention has been described in connection with specific preferred embodiments and certain working examples, it should be understood that the invention as claimed should not be unduly limited to such specific embodiments. Various modifications and variations of the described composition, method, and systems of the invention will be apparent to those skilled in the art without departing from the scope and spirit of the invention.

What is claimed is:

1. A method of detecting cervical cancer in a human, comprising the steps of:
   (a) obtaining a cervical sample from a human suspected of suffering from cervical cancer;
   (b) isolating nucleic acid from said cervical sample;
   (c) performing a molecular assay to detect an expression level of cancerous inhibitor of protein phosphatase 2A (CIP2A) in said cervical sample, said molecular assay is selected from the group consisting of quantitative reverse transcription polymerase chain reaction (qRT-PCR) and Western blot analysis;
   (d) detecting cervical cancer in said human based on said molecular assay that has a sensitivity of at least 80% and a specificity of >90%,
   wherein an increase in expression level of said CIP2A as evidenced by said molecular assay is indicative of cervical cancer in said human.

2. The method of claim 1, wherein said cervical sample is obtained with a swab.

3. The method of claim 1, wherein said cervical sample is a tissue.

4. The method of claim 1, wherein said CIP2A is a mRNA or a protein.

5. The method of claim 4, wherein said CIP2A is a mRNA.

6. The method of claim 4, wherein said CIP2A is a protein.

7. The method of claim 4, wherein said molecular assay is qRT-PCR.

8. The method of claim 4, wherein said molecular assay is Western blot analysis.

9. The method of claim 1, further comprising the step of:
   (e) detecting an expression level of a cervical cancer biomarker selected from the group consisting of Ki67, topoisomerase 2-alpha (TOP2A), minichromosome maintenance complex component 2(MCM2), minichromosome maintenance complex component 5(MCM5), $p14^{ARF}$ and $p16^{INK4a}$ in said cervical sample,
   wherein an increase in expression level of CIP2A in combination with an increase in expression level of said cervical cancer biomarker is indicative of cervical cancer in said human.

10. The method of claim 9, wherein said increase in expression level of CIP2A in combination with said increase expression level of said cervical cancer biomarker provides an assay sensitivity of at least 90%.

11. The method of claim 9, wherein said cervical cancer biomarker is Ki67.

12. The method of claim 9, wherein said cervical cancer biomarker is TOP2A.

13. The method of claim 9, wherein said cervical cancer biomarker is MCM2.

14. The method of claim 9, wherein said cervical cancer biomarker is MCM5.

15. The method of claim 9, wherein said cervical cancer biomarker is $p14^{ARF}$.

16. The method of claim 9, wherein said cervical cancer biomarker is $p16^{INK4a}$.

* * * * *